United States Patent
Le

(10) Patent No.: US 11,906,510 B2
(45) Date of Patent: Feb. 20, 2024

(54) METABOLIC PROFILING BY REVERSE-PHASE/ION-EXCHANGE MASS SPECTROMETRY

(71) Applicant: The Board of Trustees of the Leland Stanford Junior University, Stanford, CA (US)

(72) Inventor: Anthony T. Le, Stanford, CA (US)

(73) Assignee: Stanford Junior University, Stanford, CA (US)

( * ) Notice: Subject to any disclaimer, the term of this patent is extended or adjusted under 35 U.S.C. 154(b) by 155 days.

(21) Appl. No.: 17/207,295

(22) Filed: Mar. 19, 2021

(65) Prior Publication Data

US 2021/0364498 A1 Nov. 25, 2021

Related U.S. Application Data

(60) Provisional application No. 62/992,383, filed on Mar. 20, 2020.

(51) Int. Cl.
*G01N 33/50* (2006.01)
*G01N 30/72* (2006.01)
(Continued)

(52) U.S. Cl.
CPC ......... *G01N 33/5038* (2013.01); *G01N 30/06* (2013.01); *G01N 30/72* (2013.01); *G01N 2030/027* (2013.01)

(58) Field of Classification Search
CPC .... G01N 33/5038; G01N 30/06; G01N 30/72; G01N 2030/027; G01N 30/461;
(Continued)

(56) References Cited

U.S. PATENT DOCUMENTS

2013/0137185 A1* 5/2013 Holmquist .......... H01J 49/0027
436/140
2013/0280788 A1* 10/2013 Skudas ................ G01N 30/468
530/413

(Continued)

FOREIGN PATENT DOCUMENTS

WO WO-0057170 A1 * 9/2000 ....... G01N 27/44773

OTHER PUBLICATIONS

Jandera, Pavel. "Optimization of Normal-Phase and Reversed-Phase Systems for Analysis of Pesticides: Choice of the Mode of Elution—Isocratic and Gradient Elution." High Performance Liquid Chromatography in Pesticide Residue Analysis. CRC Press, 2015. 215-242. (Year: 2015).*
Opiteck, Gregory J., et al. "Comprehensive on-line LC/LC/MS of proteins." Analytical chemistry 69.8 (1997): 1518-1524. (Year: 1997).*

(Continued)

*Primary Examiner* — Jill A Warden
*Assistant Examiner* — Michael Paul Shimek
(74) *Attorney, Agent, or Firm* — Foley & Lardner LLP

(57) ABSTRACT

Disclosed herein are methods of analyzing a biological sample comprising: separating components of the biological sample via reversed-phase (RP) chromatography to obtain an elute; subjecting the elute to separation via ion-exchange (IEX) chromatography or mixed-mode IEX chromatography; and detecting the separated compounds to determine the components of the biological sample. Also disclosed are devices comprising a reversed-phase (RP) chromatography column in communication with an ion-exchange (IEX) chromatography column or mixed-mode IEX chromatography column, wherein there is no switching valve between the columns.

11 Claims, 9 Drawing Sheets

(51) Int. Cl.
G01N 30/06 (2006.01)
G01N 30/02 (2006.01)

(58) Field of Classification Search
CPC .............. G01N 33/6806; G01N 33/92; G01N 2560/00; G01N 2800/04; B01D 15/325; B01D 15/361
See application file for complete search history.

(56) References Cited

U.S. PATENT DOCUMENTS

2015/0087816 A1* 3/2015 Forrer ................. B01J 20/3257
530/417
2017/0059535 A1* 3/2017 Carrard ............. G01N 33/6848

OTHER PUBLICATIONS

Link, Andrew J., et al. "Direct analysis of protein complexes using mass spectrometry." Nature biotechnology 17.7 (1999): 676-682. (Year: 1999).*
Bruggink et al., "Combining Ion Chromatography with Mass Spectrometry and Inductively Coupled Plasma-Mass Spectrometry: Annual Review 2020," Anal. Sci Adv. 2020, 1-12.
Le et al., "Metabolic Profiling by Reversed-Phase/Ion-Exchange Mass Spectrometry," Journal of Chromatography B 1143 (2020) 122072.
Pirok et al., "Recent Developments in Two-Dimensional Liquid Chromatography: Fundamental Improvements for Practical Applications," Anal. Chem. 2019, 91, 240-263.
Stoll et al., "Two-Dimensional Liquid Chromatography: A State of the Art Tutorial," Anal. Chem. 2017, 89, 519-531.

* cited by examiner

C. Urine Samples – Negative Mode

# METABOLIC PROFILING BY REVERSE-PHASE/ION-EXCHANGE MASS SPECTROMETRY

CROSS-REFERENCE TO RELATED APPLICATIONS

This application claims the benefit of and priority to U.S. Patent Application No. 62/992,383, filed on Mar. 20, 2020, the contents of which are incorporated herein in their entirety.

STATEMENT OF GOVERNMENT SUPPORT

This invention was made with Government support under contract HD081355 awarded by the National Institutes of Health. The Government has certain rights in the invention.

BACKGROUND

The human metabolome encompasses lipids, carbohydrates, and metabolic intermediates (e.g., organic acids, amino acids, and acylcarnitines). Detection of these diverse compound classes using liquid chromatography-mass spectrometry (LC-MS) currently requires multiple chromatographic techniques. Commonly, lipidomic methods use reversed-phase (RP) chromatography, hydrophilic interaction chromatography (HILIC), or direct infusion; and glycomic methods use HILIC. Because methods based on either RP or HILIC alone can miss key metabolites, results from the independent use of these two approaches are often combined to capture and detect the full range of compounds by full-scan MS. However, this approach requires separate sample preparations for each chromatographic technique, and leads to overlapping datasets (i.e., the same metabolite being detected on both techniques) that must be meticulously curated to achieve a single, unique result set.

Various chromatographic strategies have been investigated to address limitations of the independent use of RP and HILIC. These include RP methods using mobile phase modifiers, such as ion-pairing reagents or ammonium fluoride, and columns with increased polar retention, such as C18-pentafluorophenyl (PFP) and porous graphitic carbon (Hypercarb), as well as combined RP-HILIC or HILIC-RP arrangements. While these strategies expand metabolome coverage, they are unable to resolve key pathognomonic metabolites (e.g., alloisoleucine, seen in maple syrup urine disease) without sacrificing negative mode ionization, or they require at least two LC systems to overcome mobile phase incompatibility. Ion-exchange (IEX) chromatography and mixed-mode IEX have also been investigated to widen metabolite coverage, especially to retain highly charged metabolites, but, under the conditions studied, were associated with prolonged retention of hydrophobic or highly charged compounds, or the lack of hydrophobic retention.

Alternatively, an in-line dual-column IEX-RP configuration using a single LC system has been used to increase peak capacity in proteomic applications. and the RP column would separate the remaining, less polar metabolites. By pairing RP with IEX, it was predicted that both polar and non-polar metabolites should bind to and elute from their appropriate columns, resulting in expanded metabolite coverage with one LC system.

It is against this background that a need arose to develop the embodiments described herein.

BRIEF DESCRIPTION OF THE DRAWINGS

As shown in FIG. 9, an autosampler (AS) is upstream of the two in-series columns.

As shown in FIG. 10, an autosampler (AS) is upstream of the two in-series columns.

DETAILED DESCRIPTION

Figure 1:
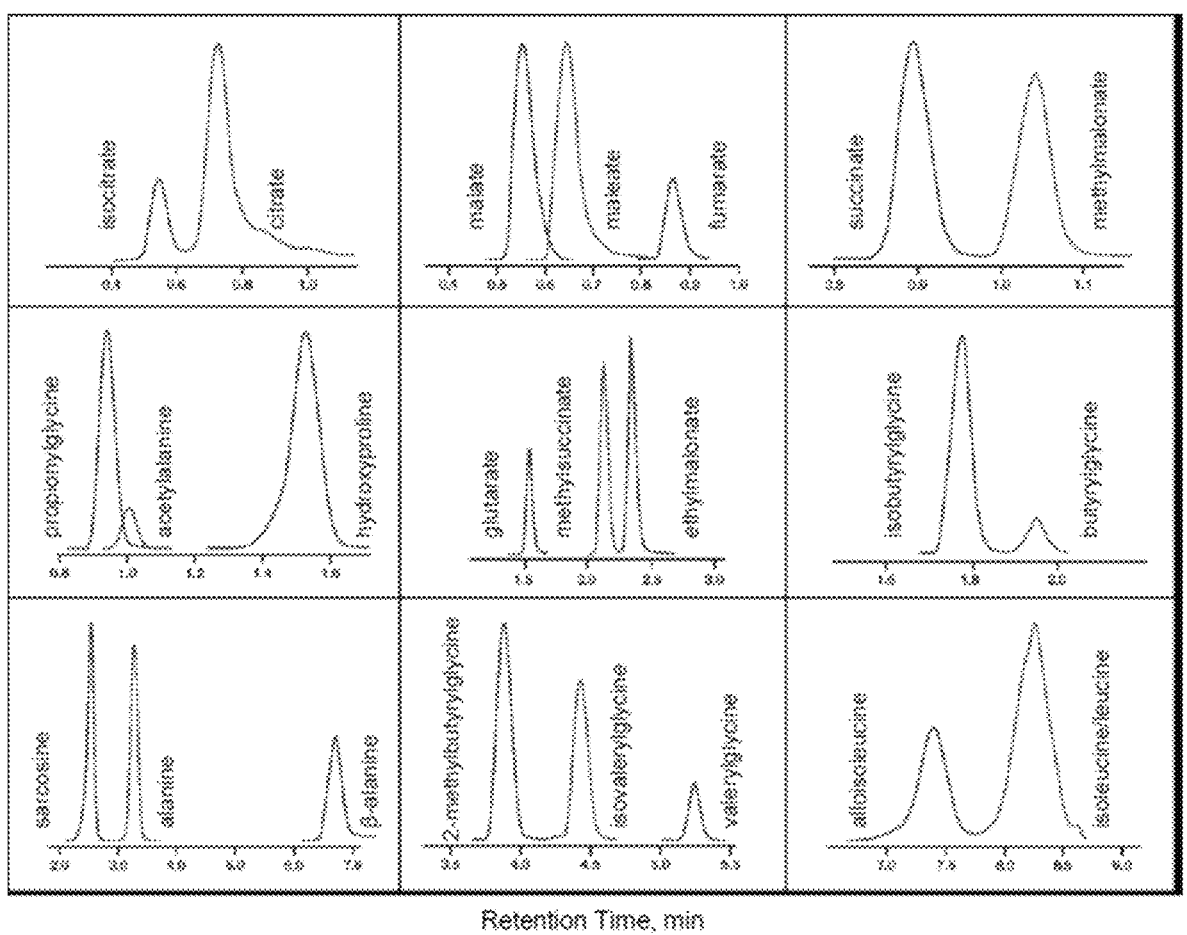
FIG. 1 shows an embodiment of the resolution of isomers. Extracted ion chromatograms of isomers commonly found in metabolic profiling. Authentic standards were used and are listed in the figure. Malic acid undergoes in-source fragmentation and can interfere with the analysis of fumaric acid or maleic acid [38]

The present disclosure includes embodiments directed to methods of analyzing a biological sample comprising: separating components of the biological sample via reversed-phase (RP) chromatography to obtain an elute; subjecting the elute to separation via ion-exchange (IEX) chromatography or mixed-mode IEX chromatography; and detecting the separated compounds to determine the components of the biological sample. In some embodiments, the biological sample is obtained from a subject having or suspected of having a metabolic disruption. In some embodiments, the biological sample is a plasma sample or a urine sample. In some embodiments, the biological sample comprises lipids, carbohydrates, and metabolic intermediates. In some embodiments, the biological sample comprises polar and non-polar metabolites. In some embodiments, the detecting step is performed using mass spectrometry. In some embodiments, the detecting step includes qualitative analysis. In some embodiments, the biological sample is separated in the RP chromatography and IEX chromatography with one solvent gradient. In some embodiments, there is no switching valve between the RP chromatography and IEX chromatography. In some embodiments, isomers of metabolites in the biological sample are separated. Representative metabolites are described in the following sections and tables.

Other embodiments include a device comprising a reversed-phase (RP) chromatography column in communication with an ion-exchange (IEX) chromatography column or mixed-mode IEX chromatography column, wherein there is no switching valve between the columns. In some embodiments, the device is configured to inject a biological sample into the reversed-phase (RP) chromatography column and the elute from the RP chromatography column is transported directly to the IEX chromatography column or mixed-mode IEX chromatography column. In some embodiments, the device is in communication with a mass spectrometer configured to measure the mass of components exiting the IEX chromatography column or mixed-mode IEX chromatography column. In some embodiments, the mass spectrometer is a triple quadrupole mass spectrometer. Representative aspects of the device are also described in the following sections and tables and figures.

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the disclosure. Changes therein and other uses which are encompassed within the spirit of the disclosure as defined by the scope of the claims will occur to those skilled in the art.

Examples

Materials and Methods
Materials

LC-MS grade methanol and formic acid were purchased from Fisher Scientific (Chino, CA). LC-MS grade water, HPLC grade acetonitrile, and HPLC grade isopropanol were purchased from VWR (Visalia, CA). LC-MS grade ammonium formate salt, high-purity ammonium hydroxide (25% v/v), and Pall Omega 3-kDa filters were purchased from Sigma-Aldrich (St. Louis, MO). The Mass Spectrometry Metabolite Library of Standards was purchased from IROA Technologies (Bolton, MA). All other standards were purchased from Sigma-Aldrich. MS calibration and reference mass solutions were purchased from Agilent Technologies (Santa Clara, CA).

Liquid Chromatography

LC separations were performed on an Agilent 1290 Quaternary LC system (Agilent Technologies, CA). The RP column, a 2.1×50 mm 1.8-micron HSS T3 (Waters, MA), was placed before the IEX column, a 2.0×30 mm 3-micron Intrada Amino Acid (Imtakt, OR). The RP column was protected with an EXP2 filter and both columns were joined with EXP2 fittings (Optimize Technologies, OR).

Chromatographic Gradient Optimization

A screening approach was used for optimization of the IEX column. The gradient table used for optimization is detailed in Table 1. The flow rate was 0.5 mL/min. The column compartment temperature was set to 45° C. The injection volume was 5 μL. The total run time was 20 minutes, inject-to-inject.

The optimized mobile phases were (A) 150 mg of ammonium formate per liter of water with 0.4% formic acid (v/v), (B) 1.2 g of ammonium formate per liter of methanol with 0.2% formic acid (v/v), and (C) water with 1% each of formic acid and ammonium hydroxide (v/v). The optimized gradient table started at 2.5% B and 0% C, then ramped to 4% B and 0% C at 3 min, 25% B and 0% C at 7 min, 95% B and 0% C at 10.8 min, 97% B and 0% C at 15.1 min, 10% B and 90% C at 15.4 min, which was held for 1.2 min, and ended with re-equilibration at the initial conditions from 16.65 to 19.5 min.

Quadrupole Time of Flight (QTOF) MS

Mass spectrometry was performed on an Agilent 6545 QTOF (Agilent Technologies, CA) equipped with dual Agilent JetStream electrospray ionization (ESI). The 6545 was operated in sensitivity-mode, with extended dynamic range enabled, and was set to acquire profile-mode data from 60-1100 m/z at a cycle time of 250 ms. The mass resolution was 11,000 at 120 m/z. Reference mass calibration solution was infused by the on-board calibrant delivery system. The source temperature was 150° C., the gas flow was 8 L/min, the nebulizer pressure was 30 psig, the sheath gas temperature was 400° C., and the sheath gas flow was 8 L/min. The capillary voltages were set to +3000 and −2500 for positive and negative polarity ionization, respectively. The LC stream was directed into the QTOF at 0.4 min. While many clinically relevant metabolites evaluated in plasma can be detected in positive polarity ionization, certain polar acids require negative polarity ionization. Therefore, to analyze plasma samples with just one injection, the MS was set to negative polarity from 0.4 to 1.85 min to detect methylmalonic acid, and then set to positive polarity for the remainder of the acquisition. Because many clinically relevant organic acids evaluated in urine ionize better or solely in negative polarity, the urine samples were acquired in negative polarity.

Samples

A test mixture consisting of five organic acids (succinic acid, methylmalonic acid, methylsuccinic acid, ethylmalonic acid, sebacic acid; all 10 μM), eight amino acids (glutamine, sarcosine, alanine, methionine, alloisoleucine, isoleucine, leucine, arginine; all 50 μM), and stearoylcarnitine (3.8 μM) was made for chromatographic method optimization and diluted, like processing a plasma sample, before analysis.

Four plasma and three urine samples from patients with metabolic disruptions were obtained as residual, de-identified specimens following routine clinical testing in the Stanford Clinical Biochemical Genetics Laboratory.

Metabolite Extraction and Analysis

To process plasma samples, 50 μL of sample was vortex mixed with 150 μL of precipitation reagent (methanol:isopropanol:formic acid 2:1:0.1% v/v/v) and centrifuged at 3° C. for 30 minutes at 17,000 xg. The supernatant was diluted 1:5 with water and analyzed. For urine, 50 μL of sample was deproteinized by ultrafiltration (3-kDa) at 3° C. for 10 minutes at 17,000 xg. The filtrate was diluted 1:2 with 1% formic acid in water (v/v) and analyzed. Two quality control (QC) samples, one plasma and one urine, were created by pooling the four plasma and the three urine samples described above. Analytical precision was assessed by injecting each sample, including the individual samples with metabolic disruptions, five times in a non-repeating sequence.

Data Analysis

Targeted qualitative data review was performed using MassHunter Qualitative 10 by searching the metabolite library of authentic standards (Agilent Technologies, CA). Run alignment, peak picking (automatic, level 4), adduct deconvolution, and feature identification using the library of authentic standards (10 ppm mass error and 0.5 min retention time error) were performed using Progenesis (Waters, MA). In both MassHunter and Progenesis, the adducts used for positive polarity analysis were [M+H], [M+NH4], and [M+Na], and the adduct used for negative polarity analysis was [M−H]. Preliminary annotation of ion features not in the library was performed using the HMDB [Nucleic Acids Res., 46 (2018) D608-D617] and KEGG [Nucleic Acids Res., 28 (2000) 27-30] plug-ins in Progenesis with search settings set to 10 ppm mass error. Unsupervised principle component analysis (PCA), with automatic log transformation and pareto scaling selected, was performed using the EZ Info Progenesis module (Umetrics, SE). For plasma samples, the negative and positive mode datasets were merged using Excel (Microsoft, WA) and then the combined dataset was imported into EZ Info for data analysis. The peak area coefficients of variation (CVs) were calculated using Excel.

Chromatographic Method Development

Two details were realized at the inception of this study. First, analytical performance would benefit from de-coupling the mixed-mode RP-IEX design. Placement of a robust RP column rated to 18,000 PSI before the IEX column, which are typically rated to 6,000 PSI, would enable faster run-times since the RP column would absorb much of the LC pressure. Furthermore, this allowed us to dictate each column's length, and thus better balance chromatographic resolution with analytical speed. Longer columns delayed both the elution of non-polar compounds captured by the RP column and highly basic metabolites captured by the IEX column (Data not shown). Second, a quaternary LC system would be necessary in some embodiments. Along with the our experience, one publication using a mixed mode C18-IEX column for small molecule separations suggested that a binary solvent system would be insufficient to control the two orthogonal stationary phases [Anal. Chem., 83 (2011) 2152-2161]. An organic gradient would be needed to control elution on the RP column and a volatile salt gradient would simultaneously be needed to control the IEX column.

Method development was focused on understanding IEX separations for small molecules. During initial screening, it was confirmed that the IEX column captured amino acids using an acidic, low salt aqueous mobile phase. Importantly, it was learned that the most basic amino acids did not elute with high salt in methanol, but did elute with high salt in water.

Fifteen combinations of ammonium formate (0, 50, 100, 150, 300 mg/L) and formic acid (0.1%, 0.2%, 0.4%) for mobile phase A were evaluated to determine their influence on the retention times and peak areas of compounds in the test mixture (Table 2). For consistency, the methanol gradient, mobile phases B and C, and the 20-minute program time were unchanged. Results demonstrate that increasing both ionic strength and formic acid did not impact the retention times of compounds strongly retained by the RP column, such as sebacic acid and stearoylcarnitine, but did decrease their sensitivities. Concurrently, increasing formic acid increased retention of polar organic acids and amino acids, but decreased the sensitivity of the polar amino acids. For both polar and neutral amino acids, increasing ionic strength decreased their retention, but did not greatly affect their sensitivity until the ionic strength increased to 300 mg of ammonium formate per liter of water. Unexpectedly, increasing ionic strength nearly baseline resolved the leucine isomers (Condition 13: 300 mg of ammonium formate per liter of water and 0.1% formic acid). However, Condition 13 could not be used due to unacceptable retention and sensitivity for other polar compounds. In sum, only Condition 12 (150 mg of ammonium formate per liter of water and 0.4% formic acid) provided resolution of succinic acid from methylmalonic acid, methylsuccinic acid from ethylmalonic acid, and alloisoleucine from isoleucine and leucine with sufficient sensitivity. For final adjustments, the proportion of methanol was decreased to 25% at 7 min for additional RP resolution and the ionic strength of mobile phase B was slightly increased for sharper amino acid peaks.

Resolution of isomers is crucial for metabolic profiling. For example, 2-methylbutyrylglycine and isovalerylglycine, both 5-carbon glycine conjugates, require separation because they represent distinct pathways in branched-chain amino acid metabolism. In another example, alloisoleucine requires separation because it is pathognomonic for maple syrup urine disease. FIG. 1 shows the separation of select isomers relevant to human metabolism. The separation of additional isomers is provided in the library (Table 3).

The limited commercial selection of similar IEX columns compatible with organic solvents severely limited exploration of the RP-IEX dynamic. Although the Imtakt Intrada Amino Acid column chemistry is proprietary, it is possible that it predominately consists of negatively charged functional groups that can capture the positively charged amino acids. Attempts to separate amino acids using the HP-SCX column from Sepax Technologies (Newark, DE) resulted in excessive retention of many amino acids. Therefore, the synthesis of a more optimal IEX stationary phase represents a clear approach to increasing chromatographic performance.

Metabolite Library

Figure 2:
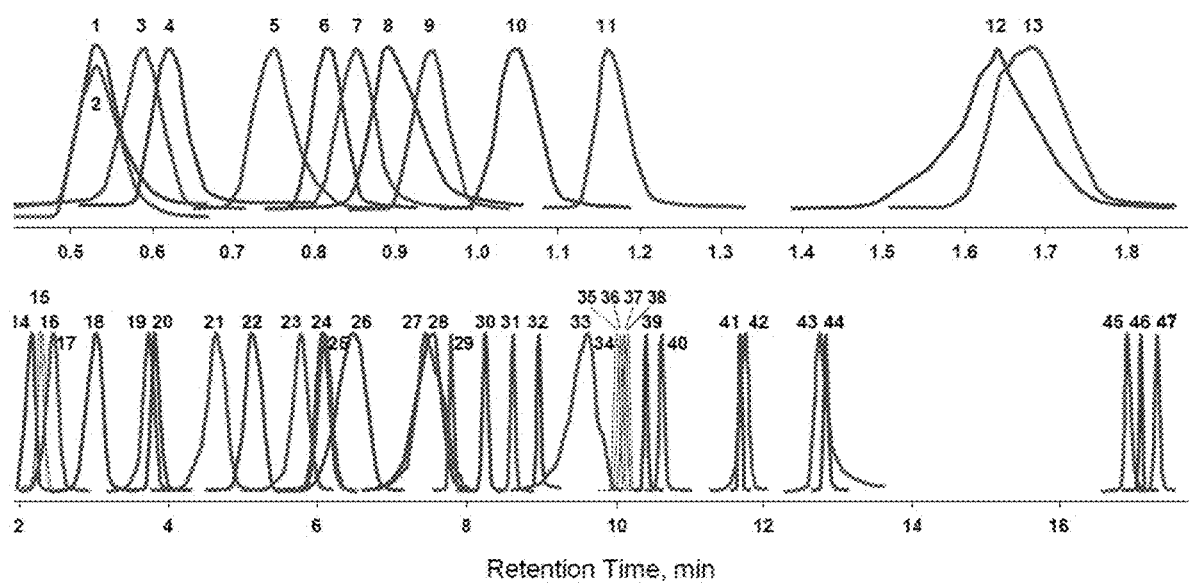
FIG. 2 shows an embodiment of the separation of polar and non-polar metabolites. Overlaid extracted ion chromatograms of standards demonstrate the wide-polarity range of compounds that can be separated by this RP-IEX method. (1) uracil, (2) orotic acid, (3) 2-ketoglutaric acid, (4) acetylglycine, (5) uric acid, (6) pyroglutamic acid, (7) uracil 5-carboxylic acid, (8) adenosine monophosphate, (9) propionylglycine, (10) xanthine, (11) 2-hydroxybutyric acid, (12) aspartic acid, (13) cyclic adenosine monophosphate, (14) asparagine, (15) glutamic acid, (16) threonine, (17) glutamine, (18) proline, (19) guanosine, (20) adipic acid, (21) citrulline, (22) methionine, (23) cysteine, (24) tyrosine, (25) phenylpyruvic acid, (26) homocitrulline, (27) guanidinoacetic acid, (28) creatine, (29) biotin, (30) hexanoylglycine, (31) phenylpropionylglycine, (32) suberic acid, (33) adenosine, (34) carnitine, (35) glutarylcarnitine, (36) deoxycytidine, (37) methylthioadenosine, (38) tryptophan, (39) propionylcarnitine, (40) cystine, (41) cholic acid, serotonin, (43) argininosuccinic acid, (44) stearoylcarnitine, (45) histidine, (46) lysine, and (47) arginine. Preliminary annotations of plasma samples show that lipids might elute between 13 to 16 min (Table 5).

A library with 397 metabolites was generated using authentic standards (Table 3). This method captures a wide polarity-range of analytes, including acylcarnitines, amino acids, bile acids, nucleosides, organic acids, steroid hormones, and vitamin cofactors (FIG. 2). Because it captures compounds based on both hydrophobicity and charge, two main chemical properties governing retention, this chromatographic arrangement likely can retain many additional compounds. Nonetheless, sugars and compounds with multiple phosphate groups, which are negatively affected by trace metals in the LC system [J. Sep. Sci., 28 (2005) 1823-1830], were not retained by this method. Studies are underway to address this limitation.

Metabolite Detection with Human Samples

Figure 7A:
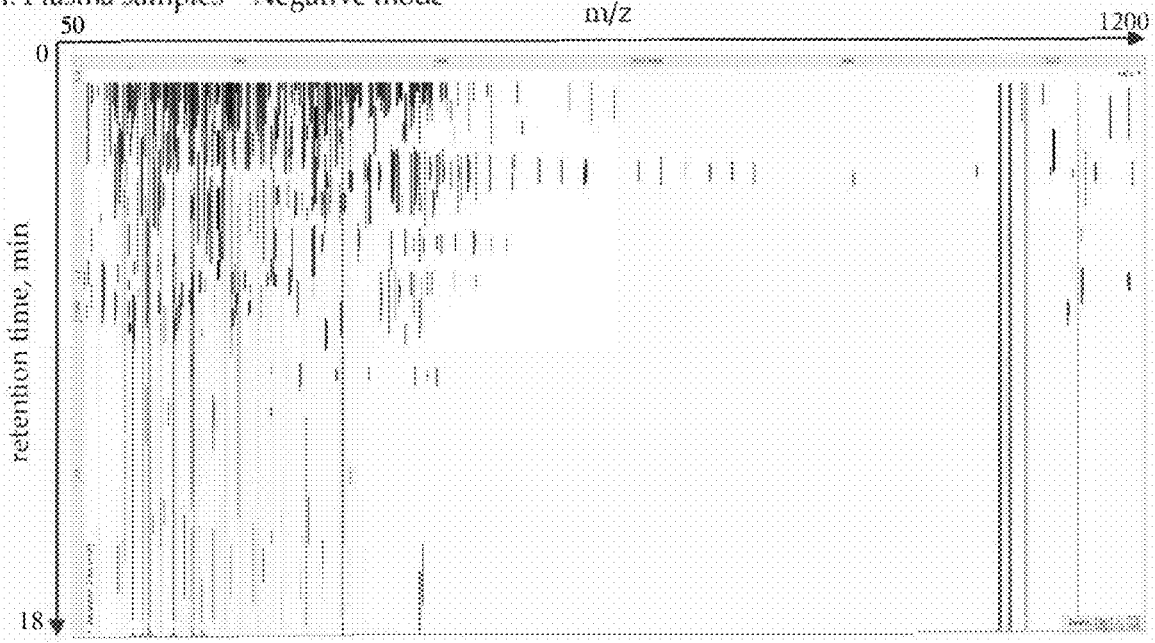
FIG. 7 shows an embodiment of ion intensity maps from Progenesis for the plasma samples, acquired with one injection beginning with (a) negative mode (480 ions) and then switching to (b) positive mode (7092 ions), and for the (c) urine samples acquired in negative mode (7371 ions) are shown. The detected ion features are indicated in blue.
Figure 7B:
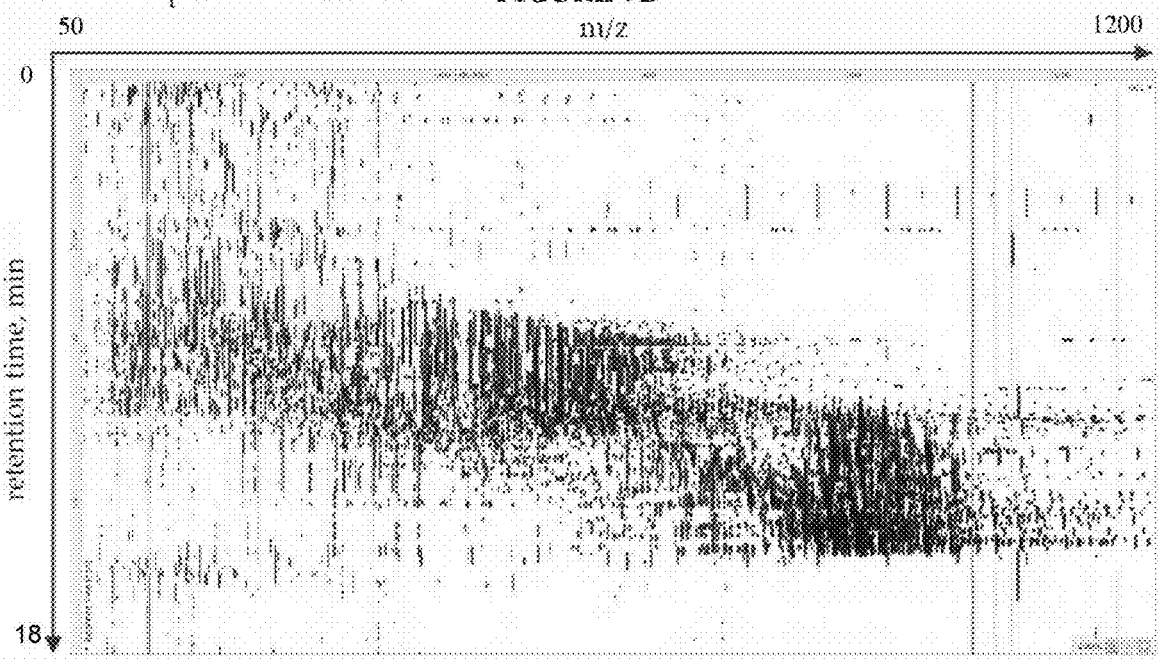
Figure 7C:
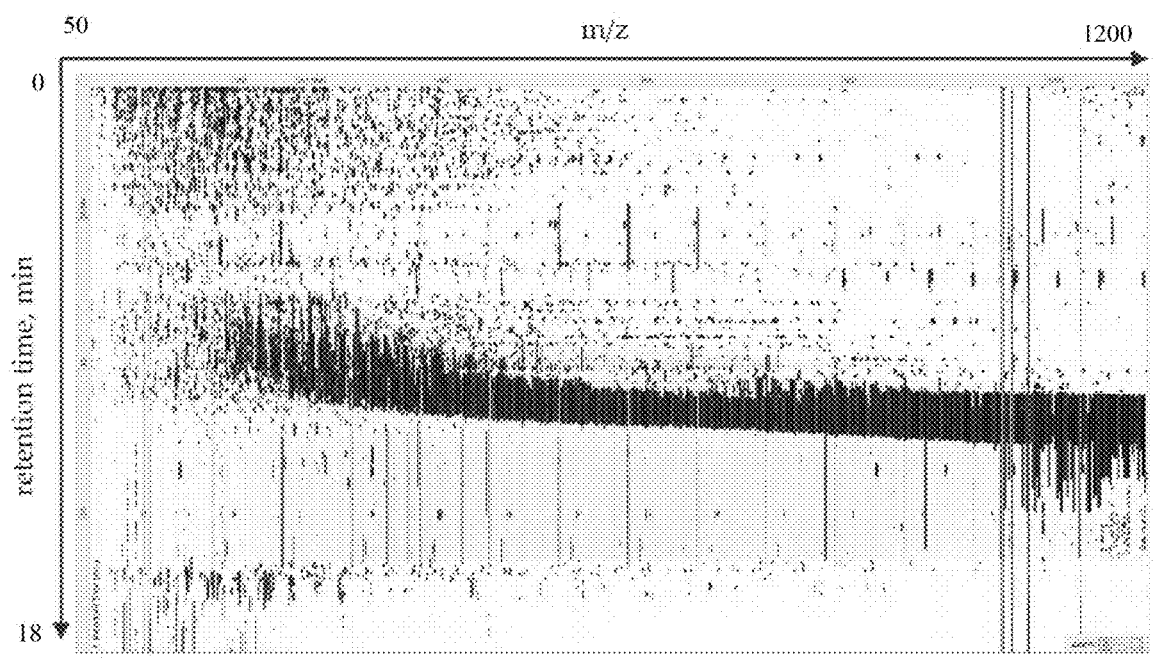
Figure 8:
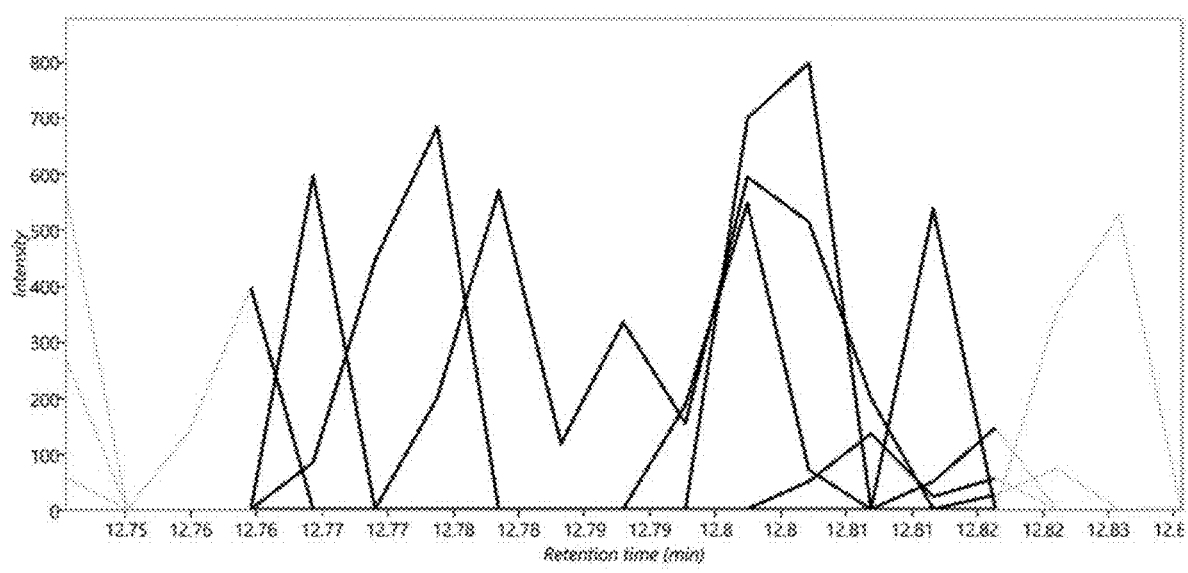
FIG. 8 shows an embodiment of the method precision evaluated using the plasma QC samples. The chromatogram shows peak integrations (black traces; all five injections are shown) of an ion feature that were discarded from the precision study in FIG. 5. Of the five replicate injections, this feature had a maximum abundance of 83.
Figure 9:
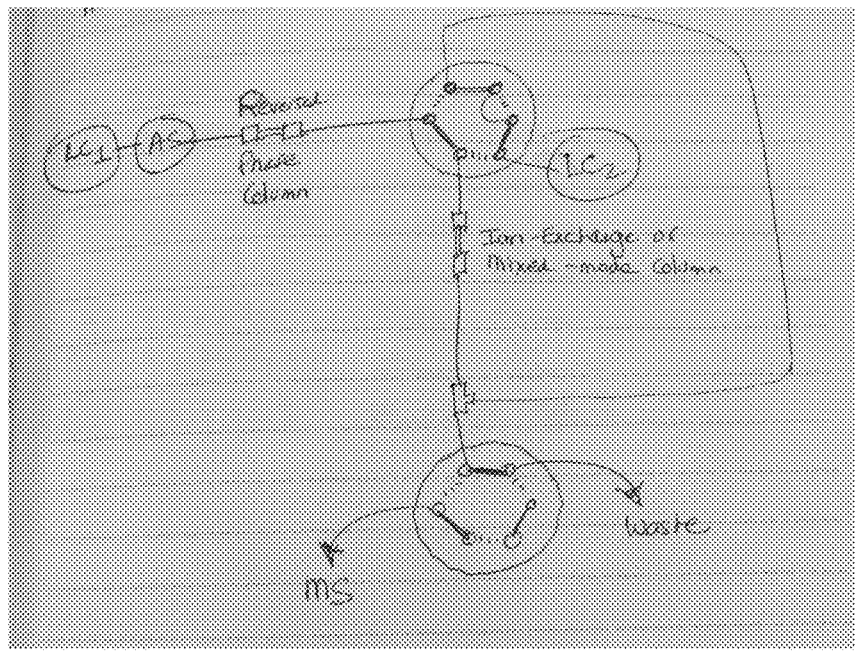
FIG. 9 shows an embodiment of a device used for the present methods with a switching valve between the two columns. In some embodiments this type of device is suitable for universal metabolomic analysis with two in-series columns with different functionalities by LC-MS/MS.
Figure 10:
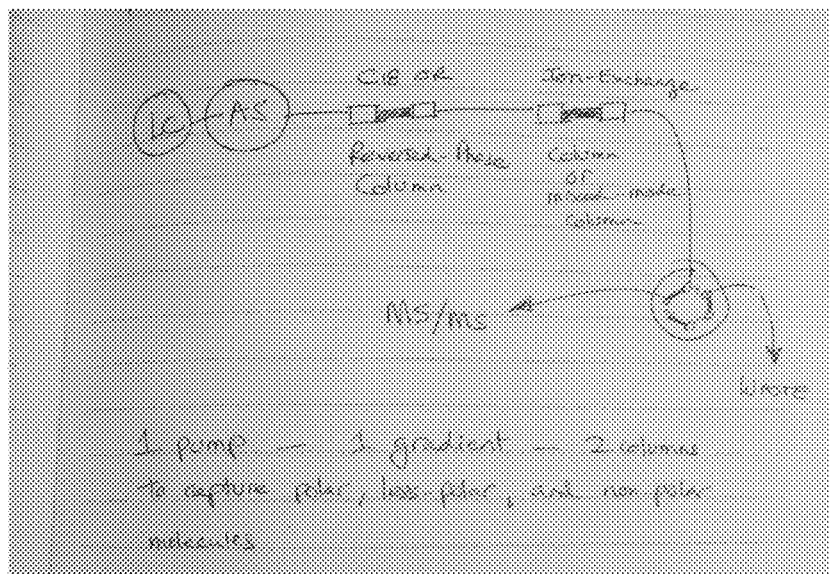
FIG. 10 shows an embodiment of a device used for the present methods without a switching valve between the two columns. In some embodiments this type of device is suitable for universal metabolomic analysis with two in-series columns with different functionalities by LC-MS/MS.
Figure 11:
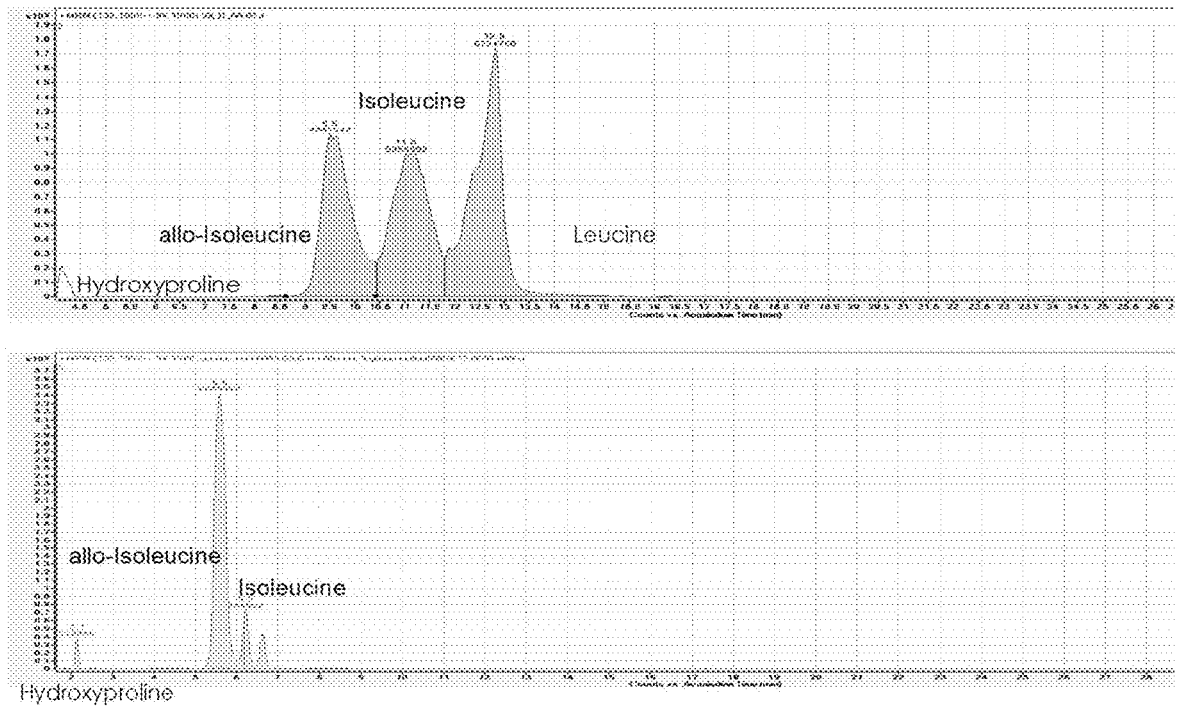
FIG. 11 shows the separation of isomers of leucine using embodiments of this disclosure.
Figure 12:
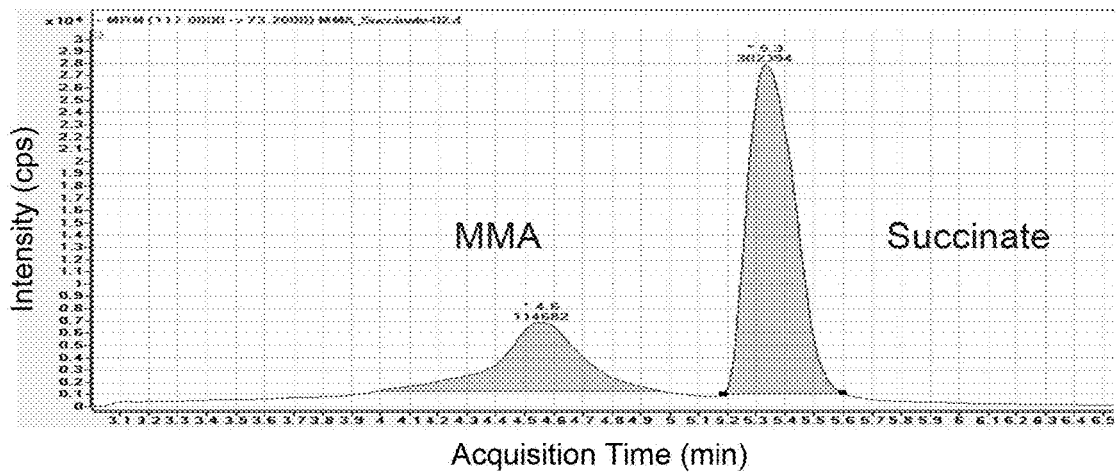
FIG. 12 shows the separation of MMA and succinate using embodiments of this disclosure.

Clinical metabolic profiling is typically performed using plasma and urine samples, both containing metabolites that require both positive and negative mode ionization. Since certain embodiments of the method does not use ion-pairing reagents, both ionization polarities can be used. Overall ion feature detection at clinically relevant concentrations was evaluated by analyzing plasma and urine samples with specific metabolic disruptions, as well as corresponding plasma or urine QC pools. Samples were selected based on the presence of clinically relevant polar and non-polar metabolites, ranging from methylmalonic acid to alloisoleucine to stearoylcarnitine. In total, Progenesis detected 7,572 ion features for the plasma samples and 7,371 ion features for the urine samples (FIG. 7). However, manual peak review showed that ion features with median peak areas below 100 (2,127 features for plasma and 3,260 features for urine) were essentially noise (FIG. 8). In total, 5,445 and 4,111 ion features for the plasma and urine groups respectively were not marked as noise.

Metabolite identification in the plasma and urine QC samples, which contained pathologic compounds at diluted concentrations and endogenous compounds at physiologic concentrations, using a library of authentic standards revealed 88 and 82 metabolites, respectively (Table 4). This method detected metabolites such as methylmalonic acid, glutamine, glycine, citrulline, methionine, alloisoleucine, arginine, creatine, carnitine, propionylcarnitine, stearoylcarnitine, 2-methylcitric acid, propionylglycine, 2-methylbutyrylglycine, 3-methylcrotonylglycine, adipic acid, suberic acid, and glutaric acid. Notably, plasma samples were evaluated at a 1:20 final dilution to reflect simple and rapid sample processing desired by clinical laboratories. Despite the dilution factors, the peak areas for most metabolites still ranged from 104 to 106. Should higher sensitivity be necessary, an evaporation step could be incorporated.

While in some embodiments the method was not intended for lipidomic applications, many semi-lipophilic metabolites were detected in some embodiments. Stearoylcarnitine is one the most non-polar metabolic intermediates in the library and has a retention time of 12.8 min. Therefore, to elute additional semi-lipophilic metabolites, RP regeneration was extended to 15.1 min. An identification search of m/z features in plasma (FIG. 7b) eluting between minutes 13 and 16 mainly resulted in preliminary annotations for lipids. For example, six lipids were listed as potential annotations for a feature eluting at 14.47 min with a m/z of 844.5093 (Table 5). After five non-sequential replicate injections, this feature had a peak area CV of 4.7% (average peak area=29, 235), indicating consistent elution. Based on these observations, using isopropanol in the fourth solvent channel may expand lipid coverage.

Data Quality of the LC-QTOF Method

Figure 3:
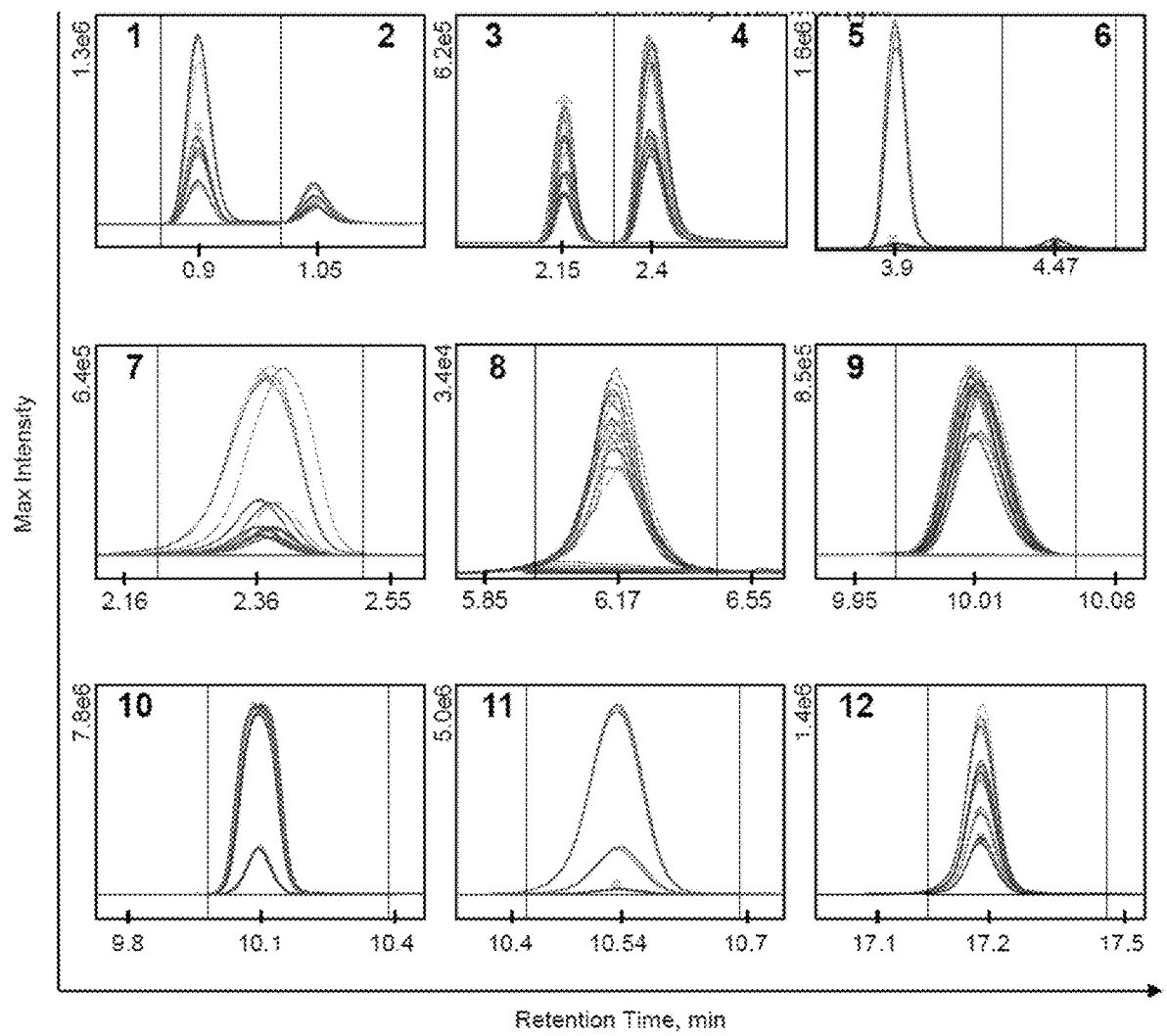
FIG. 3 shows an embodiment of Retention Time Stability. Retention time stability was evaluated by injecting each sample five times. For eachanalyte, all injections were overlaid (plasma: n=25; urine: n=20). (1) succinic acid, (2) methylmalonic acid, (3) methylsuccinic acid, (4) ethylmalonic acid, (5) 2-methylbutyrylglycine, and (6) isovalerylglycine were from urine samples, and (7) glutamic acid, (8) tyrosine, (9) alloisoleucine, (10) isoleucine/leucine, (11) phenylalanine, and (12) propionylcarnitine were from plasma samples.

Consistent retention times and compound ionization can be critical for peak alignment and downstream reporting quality [Metabolomics, 14 (2018) 1-17]. Within-run analytical precision was evaluated by injecting each sample five times, totaling 45 injections. FIG. 3 shows overlaid extracted ion chromatograms of select compounds for all injections, demonstrating consistent retention times and peak areas throughout the acquisition. Retention times remained within a 0.5-minute retention time window at least one month after generation of the in-house library, indicating good retention time stability.

Figure 4:
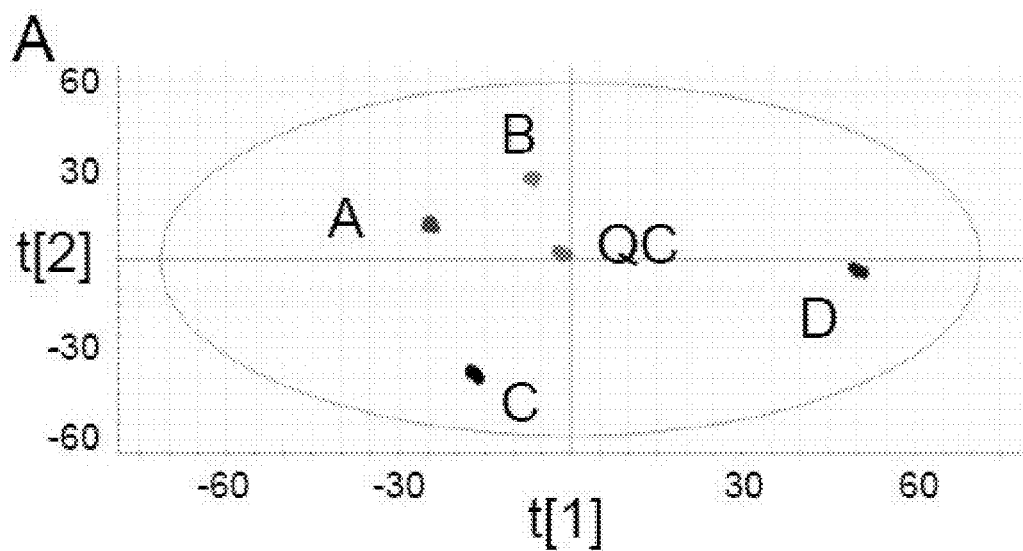
FIG. 4 shows an embodiment of the assessment of data quality by principal component analysis. Data quality was evaluated by unsupervised principal component analysis. (A) Five plasma and (B) four urine samples were each injected five times. Principal components one (t[1]) and two (t[2]) are shown. Groups A-G each represent individual metabolic diseases.
Figure 4:
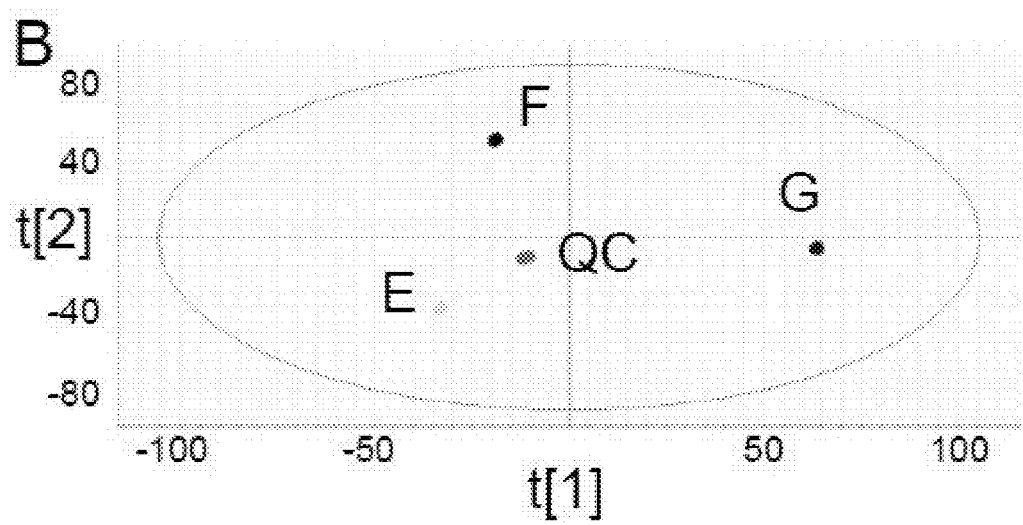
Figure 5:
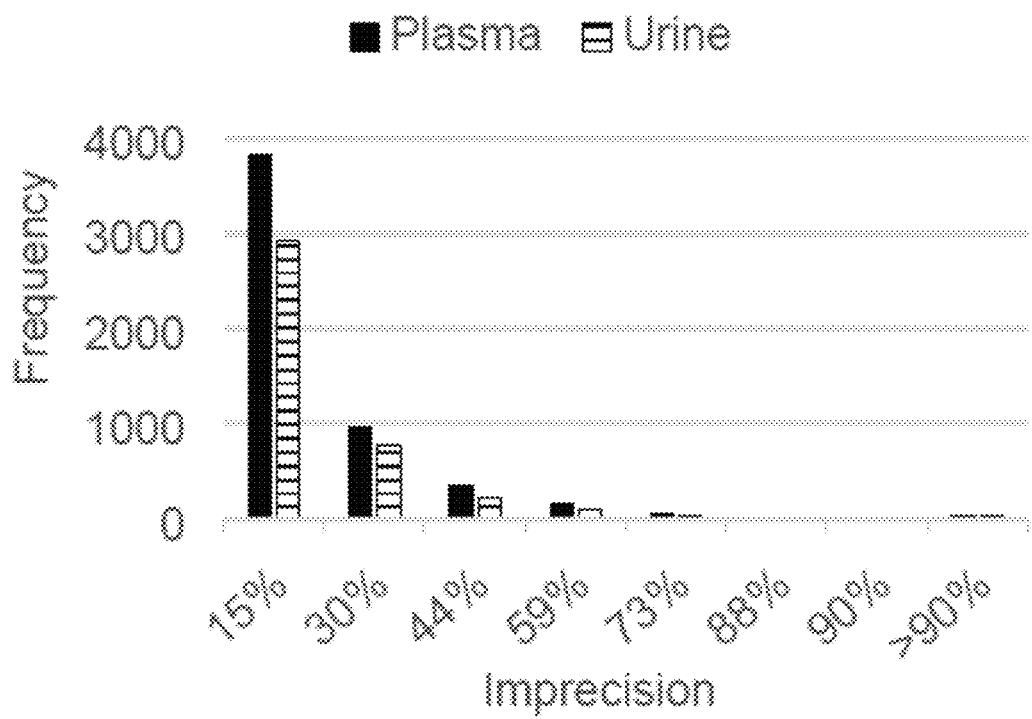
FIG. 5 shows an embodiment of the frequency of peak area precision. Histogram of peak area CVs calculated from five replicate injections of the plasma (black) or urine (stripe) QC sample. The distributions were calculated from 5,445 and 4,111 features for plasma and urine, respectively.
Figure 6:
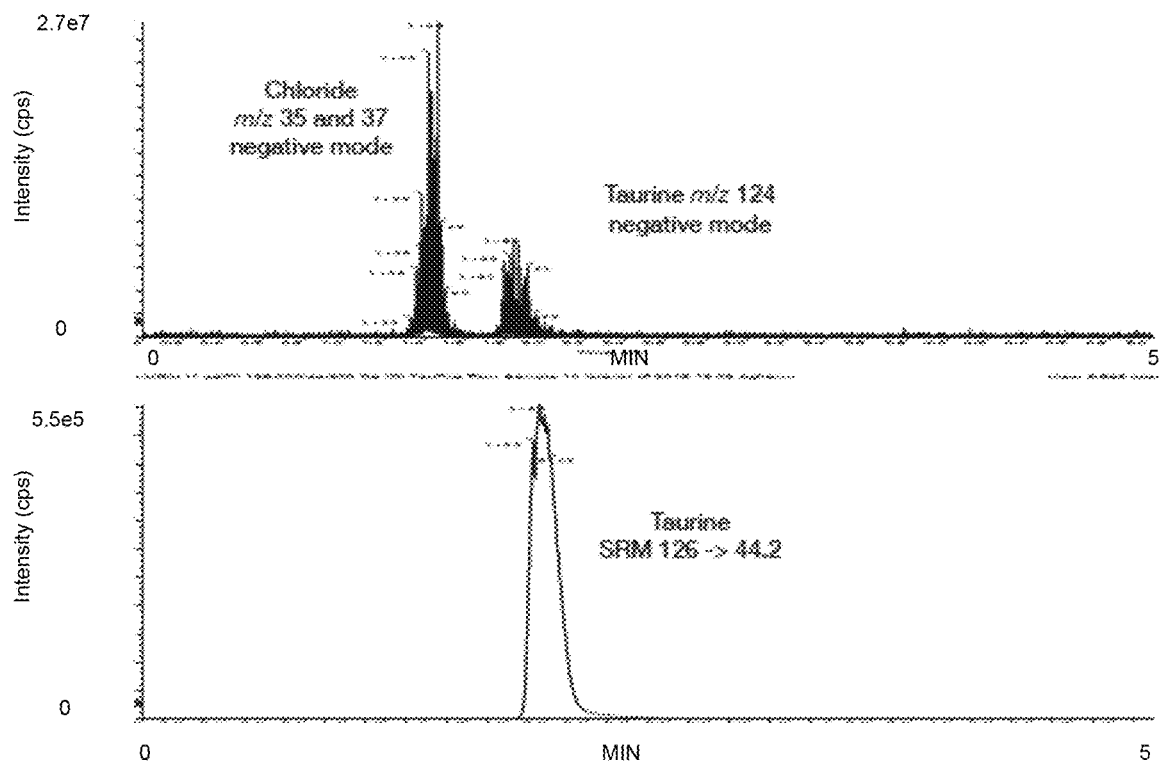
FIG. 6 shows an embodiment of the separation of chloride and taurine.

Next, overall within-run analytical data quality was assessed by unsupervised PCA, including features marked as noise. FIG. 4 shows that the replicate injections overlap, indicating excellent analytical quality. Precision was assessed by calculating the peak area CVs of the QC samples, excluding median peak areas below 100 (FIG. 5). Of the remaining 5,445 features in the plasma QC group, 88% had CVs<30% and 79% had CVs<20%. Of the remaining 4,111 features in the urine QC group, 91% had CVs<30% and 81% had CVs<20%. This precision meets current QC guidelines and is comparable to current RP-HRMS methods, where 70-90% of the features detected in the QC group have CVs<30% [Bioanalysis, 4 (2012) 2249-2264.].

While the two columns contain distinct stationary phases, the possibility of disturbed metabolite elution due to the in-line column configuration was investigated by analyzing the peak area precision of select acylcarnitines, which are first retained by the RP column and then go through the IEX column, and amino acids, which pass through the RP column and are retained by the IEX column (Table 6). The plasma QC data showed CVs less than 4% for propionylcarnitine, palmitoylcarnitine, and stearoylcarnitine, suggesting that the IEX column is unlikely to interfere with the elution of compounds first retained by the RP column. For amino acids, the peak area CVs ranged from 1.7% to 6.9% for glutamine, alanine, citrulline, methionine, alloisoleucine, leucine, and tryptophan, demonstrating that the RP column does not interfere with the movement of amino acids onto the IEX column. This data and the high-quality peaks presented in FIGS. 1 and 2 suggest that the in-line column configuration is unlikely to interfere with metabolite elution.

CONCLUSION

The chromatographic design outlined here underscores the critical role of chromatography in metabolic profiling. In-line RP-IEX chromatography enables the separation of a wide polarity range of clinically relevant metabolic intermediates, including isomers, in 20-minutes with one LC-MS system. Notably, the simple RP-IEX setup retains and separates amino acids, acylcarnitines, and organic acids, which currently require multiple LC systems or independent RP and HILIC analyses. Each column can be independently controlled and behaves synergistically to increase the number of detected metabolites. The method showed high analytical quality and provided suitable sensitivity for human plasma and urine samples. Because ion-pairing reagents are not used, the MS system can be used in both negative and positive polarity. For targeted applications, the LC method can be coupled to a triple quadrupole mass spectrometer, which can provide enhanced sensitivity, precision, dynamic range, and rapid polarity switching.

Gradient Program Used for LC Optimization

Mobile phase A was optimized as indicated in Table 2. Mobile phase B contained 1 g of ammoniumformate per liter of methanol and 0.2% formic acid (v/v) and mobile phase C contained water with 1% each of formic acid and ammonium hydroxide (v/v).

TABLE 1

Gradient program used for LC optimization

| Time, min | % A | % B | % C | % D |
|---|---|---|---|---|
| 0 | 97.5 | 2.5 | 0 | 0 |
| 3 | 96 | 4 | 0 | 0 |
| 8 | 65 | 35 | 0 | 0 |
| 10.9 | 5 | 95 | 0 | 0 |
| 15.1 | 3 | 97 | 0 | 0 |
| 15.5 | 0 | 10 | 90 | 0 |
| 16.6 | 0 | 10 | 90 | 0 |
| 16.65 | 97.5 | 2.5 | 0 | 0 |
| 19.5 | 97.5 | 2.5 | 0 | 0 |

LC Optimization Results

The levels of ionic strength and formic acid were optimized for mobile phase A by tracking retention time (minutes) and peak area (in millions). LC conditions used for the optimization are detailed in Table 1.

For peaks without baseline resolution, the retention times are reported together and the peak areas are summed. AF, ammonium formate salt; formic acid, FA; SA, succinic acid; MMA, methylmalonic acid; MS, methylsuccinic acid; EMA, ethylmalonic acid; Seb, sebacic acid; Gln, glutamine; Sarc, sarcosine; Ala, alanine; Met, methionine; Aile, alloisoleucine; Ile, isoleucine; Leu, leucine; Arg, arginine; C18, stearoylcarnitine.

TABLE 2

LC Optimization results
Mobile Phase A Retention time, min

| Condition | AF (mg/L) | FA % (v/v) | SA | MMA | MS | EMA | Seb | Gln | Sarc | Ala | Met | Aile | Ile | Leu | Arg | C18 |
|---|---|---|---|---|---|---|---|---|---|---|---|---|---|---|---|---|
| 1 | 0 | 0.1 | 0.89 | 0.96 | 2.2 | | 10.6 | 2.8 | 2.9 | 4.2 | 7.3 | | 11.4 | | 17.4 | 13.1 |
| 2 | 0 | 0.2 | 0.90 | 1.00 | 2.3 | 2.6 | 10.6 | 3.1 | 3.4 | 4.4 | 8.0 | | 11.8 | | 17.4 | 13.1 |
| 3 | 0 | 0.4 | 0.88 | 1.10 | 2.5 | 2.8 | 10.6 | 3.3 | 3.3 | 4.4 | 7.8 | | 11.9 | | 17.4 | 13.1 |
| 4 | 50 | 0.1 | 0.90 | | 2.1 | | 10.6 | 2.4 | 2.4 | 3.5 | 6.2 | 9.7 | 10.8 | | 17.4 | 13.1 |
| 5 | 50 | 0.2 | 0.90 | 1.00 | 2.2 | 2.5 | 10.6 | 2.7 | 2.8 | 4.0 | 6.8 | 10.2 | 11.1 | | 17.4 | 13.1 |
| 6 | 50 | 0.4 | 0.88 | 1.00 | 2.4 | 2.7 | 10.6 | 3.0 | 3.0 | 4.1 | 6.8 | 10.0 | 11.4 | | 17.4 | 13.1 |
| 7 | 100 | 0.1 | 0.90 | | 1.8 | | 10.6 | 2.1 | 2.1 | 3.1 | 5.3 | 7.8 | 9.1 | | 17.4 | 13.1 |
| 8 | 100 | 0.2 | 0.90 | | 2.2 | | 10.6 | 2.7 | 2.7 | 3.7 | 5.8 | 8.6 | 9.9 | | 17.4 | 13.1 |
| 9 | 100 | 0.4 | 0.88 | 1.00 | 2.4 | | 10.6 | 2.9 | 2.9 | 3.8 | 5.6 | 8.8 | 9.9 | | 17.4 | 13.1 |
| 10 | 150 | 0.1 | 0.89 | | 1.9 | 2.2 | 10.6 | 1.9 | 1.9 | 2.7 | 4.6 | 6.5 | 7.4 | | 17.4 | 13.1 |
| 11 | 150 | 0.2 | 0.89 | 0.96 | 2.1 | | 10.6 | 2.2 | 2.2 | 3.1 | 5.1 | 7.4 | 8.4 | | 17.4 | 13.1 |
| 12 | 150 | 0.4 | 0.88 | 1.00 | 2.1 | 2.3 | 10.6 | 2.5 | 2.6 | 3.4 | 5.1 | 7.7 | 8.5 | | 17.4 | 13.1 |
| 13 | 300 | 0.1 | 0.83 | | 1.7 | 2.0 | 10.6 | 1.3 | 1.3 | 1.7 | 2.7 | 3.9 | 4.2 | 4.5 | 17.4 | 13.1 |
| 14 | 300 | 0.2 | 0.92 | | 2.0 | | 10.6 | 1.6 | 1.6 | 2.1 | 3.9 | 5.1 | | 5.7 | 17.4 | 13.1 |
| 15 | 300 | 0.4 | 0.87 | 0.97 | 2.0 | 2.2 | 10.6 | 1.9 | 1.9 | 2.5 | 4.1 | 5.7 | 6.0 | 6.6 | 17.4 | 13.1 |
| 1 | 0 | 0.1 | 0.17 | 0.99 | 7.40 | | 0.46 | 4.00 | 2.94 | 1.66 | 1.14 | | 0.22 | | 0.65 | 5.21 |
| 2 | 0 | 0.2 | 0.18 | 0.99 | 3.51 | 0.48 | 0.35 | 0.90 | 1.35 | 0.33 | 0.41 | | 0.11 | | 1.70 | 4.30 |
| 3 | 0 | 0.4 | 0.19 | 0.87 | 1.40 | 0.19 | 0.34 | 0.34 | 0.84 | 0.14 | 0.20 | | 0.62 | | 1.80 | 3.70 |
| 4 | 50 | 0.1 | | 1.30 | 3.64 | | 0.48 | 3.34 | 2.45 | 1.09 | 1.00 | 0.61 | 0.95 | | 2.00 | 3.34 |
| 5 | 50 | 0.2 | 0.26 | 1.08 | 5.54 | 0.59 | 0.07 | 1.07 | 1.41 | 0.34 | 0.44 | 0.26 | 0.11 | | 1.89 | 3.05 |
| 6 | 50 | 0.4 | 0.24 | 0.85 | 0.92 | 0.27 | 0.32 | 0.35 | 0.87 | 0.15 | 0.25 | 0.60 | 0.50 | | 1.90 | 3.20 |
| 7 | 100 | 0.1 | | 1.46 | 4.55 | | 0.04 | 3.50 | 2.64 | 1.17 | 1.08 | 0.75 | 1.22 | | 0.90 | 1.60 |
| 8 | 100 | 0.2 | 0.28 | 1.19 | 2.50 | | 0.05 | 0.88 | 1.44 | 0.32 | 0.43 | 0.21 | 1.02 | | 2.10 | 1.43 |
| 9 | 100 | 0.4 | 0.23 | 0.87 | 1.62 | | 0.30 | 0.33 | 0.90 | 0.14 | 0.31 | 0.83 | 0.91 | | 2.10 | 1.41 |
| 10 | 150 | 0.1 | | 1.14 | 6.75 | 3.47 | 0.05 | 2.98 | 2.14 | 0.85 | 0.69 | 0.54 | 1.04 | | 1.88 | 1.09 |
| 11 | 150 | 0.2 | 0.24 | 1 | 7.37 | | 0.04 | 1.00 | 1.31 | 0.28 | 0.37 | 0.31 | 0.85 | | 1.79 | 1.25 |
| 12 | 150 | 0.4 | 0.24 | 0.8 | 0.20 | 0.34 | 0.04 | 0.30 | 0.79 | 0.12 | 0.25 | 0.62 | 0.83 | | 1.90 | 1.05 |
| 13 | 300 | 0.1 | | 1.09 | 0.94 | 0.21 | 0.09 | 1.71 | 1.56 | 0.39 | 0.68 | 0.57 | 0.48 | 0.80 | 1.87 | 0.87 |
| 14 | 300 | 0.2 | | 1.2 | 0.43 | | 0.09 | 0.48 | 0.92 | 0.13 | 0.28 | 0.80 | | 0.29 | 0.80 | 0.48 |
| 15 | 300 | 0.4 | 0.24 | 0.45 | 0.15 | | 0.08 | 0.18 | 0.60 | 0.09 | 0.26 | 0.42 | 0.52 | 0.90 | 1.30 | 0.51 |

TABLE 3

Metabolite library
Authentic standards were injected to generate a retention time library for this method.

| Name | Formula | Mass | Retention Time, min |
|---|---|---|---|
| cysteic acid | C3H7NO5S | 169.004 | 0.42 |
| gluconolactone | C6H10O6 | 178.048 | 0.42 |
| monoethylmalonic acid | C5H8O4 | 132.042 | 0.42 |
| n-acetylneuraminic acid | C11H19NO9 | 309.106 | 0.42 |
| phosphoserine | C3H8NO6P | 185.009 | 0.42 |
| rhamnose | C6H12O5 | 164.068 | 0.42 |
| saccharic acid | C6H10O8 | 210.038 | 0.42 |
| sulfocysteine | C3H7NO5S2 | 200.976 | 0.42 |
| taurine | C2H7NO3S | 125.014 | 0.42 |
| glucuronic acid | C6H10O7 | 194.043 | 0.43 |
| mesoxalate | C3H2O5 | 117.990 | 0.43 |
| uridine diphosphate glucose | C15H24N2O17P2 | 566.055 | 0.43 |
| gluconic acid | C6H12O7 | 196.058 | 0.44 |
| galactaric acid | C6H10O8 | 210.038 | 0.45 |

TABLE 3-continued

Metabolite library
Authentic standards were injected to generate a retention time library for this method.

| Name | Formula | Mass | Retention Time, min |
|---|---|---|---|
| uridine diphosphate-n-acetylgalactosamine | C17H27N3O17P2 | 607.082 | 0.45 |
| uridine diphosphate-n-acetylglucosamine | C17H27N3O17P2 | 607.082 | 0.45 |
| orotic acid | C5H4N2O4 | 156.017 | 0.47 |
| meso-tartaric acid | C4H6O6 | 150.016 | 0.49 |
| n-acetylmannosamine | C8H15NO6 | 221.090 | 0.49 |
| adp-glucose | C16H25N5O15P2 | 589.082 | 0.50 |
| dihydroorotic acid | C5H6N2O4 | 158.033 | 0.50 |
| n-acetylgalactosamine | C8H15NO6 | 221.090 | 0.50 |
| n-formylglycine | C3H5NO3 | 103.027 | 0.50 |
| phosphoethanolamine | C2H8NO4P | 141.019 | 0.50 |
| quinic acid | C7H12O6 | 192.063 | 0.50 |
| uracil | C4H4N2O2 | 112.027 | 0.50 |
| uridine monophosphate | C9H13N2O9P | 324.036 | 0.50 |
| malonic acid | C3H4O4 | 104.011 | 0.51 |
| isocitric acid | C6H8O7 | 192.027 | 0.55 |
| malic acid | C4H6O5 | 134.022 | 0.55 |
| n-acetylasparagine | C6H10N2O4 | 174.064 | 0.55 |
| 2-ketoglutaric acid | C5H6O5 | 146.022 | 0.55 |
| shikimic acid | C7H10O5 | 174.053 | 0.57 |
| acetylglycine | C4H7NO3 | 117.043 | 0.60 |
| glucosamine 6-phosphate | C6H14NO8P | 259.046 | 0.60 |
| pyruvic acid | C3H4O3 | 88.016 | 0.60 |
| inosine monophosphate | C10H13N4O8P | 348.047 | 0.62 |
| ureidopropionic acid | C4H8N2O3 | 132.053 | 0.63 |
| 2-propenoic acid | C3H4O2 | 72.021 | 0.64 |
| lactic acid | C3H6O3 | 90.032 | 0.64 |
| maleic acid | C4H4O4 | 116.011 | 0.64 |
| phosphorylcholine | C5H14NO4P | 183.066 | 0.64 |
| xanthosine-monophosphate | C10H13N4O9P | 364.042 | 0.64 |
| 3-dehydroshikimic acid | C7H8O5 | 172.037 | 0.65 |
| maleamic acid | C4H5NO3 | 115.027 | 0.65 |
| nicotinamide mononucleotide | C11H15N2O8P | 334.057 | 0.65 |
| n-acetylaspartic acid | C6H9NO5 | 175.048 | 0.67 |
| 5-aminoimidazole-4-carboxamide ribonucleotide | C9H15N4O8P | 338.063 | 0.68 |
| dtdp-d-glucose | C16H26N2O16P2 | 564.076 | 0.69 |
| guanosine monophosphate | C10H14N5O8P | 363.058 | 0.70 |
| 3,4 dihydroxymandelate | C8H8O5 | 184.037 | 0.73 |
| uric acid | C5H4N4O3 | 168.028 | 0.73 |
| citric acid | C6H8O7 | 192.027 | 0.75 |
| quinolinic acid | C7H5NO4 | 167.022 | 0.75 |
| 2-oxoadipic acid | C6H8O5 | 160.037 | 0.77 |
| 3,4-dihydroxyphenylglycol | C8H10O4 | 170.058 | 0.82 |
| aniline-2-sulfonate | C6H7NO3S | 173.015 | 0.83 |
| deoxycytidine monophosphate | C9H14N3O7P | 307.057 | 0.83 |
| pyroglutamic acid | C5H7NO3 | 129.043 | 0.83 |
| 2-methylmaleic acid | C5H6O4 | 130.027 | 0.84 |
| succinic acid | C4H6O4 | 118.027 | 0.85 |
| uracil 5-carboxylic acid | C5H4N2O4 | 156.017 | 0.85 |
| fumaric acid | C4H4O4 | 116.011 | 0.86 |
| mevalolactone | C6H10O3 | 130.063 | 0.87 |
| mevalonic acid | C6H12O4 | 148.074 | 0.88 |
| monomethylglutaric acid | C6H10O4 | 146.058 | 0.88 |
| n-acetylglutamic acid | C7H11NO5 | 189.064 | 0.88 |
| ketoleucine | C6H10O3 | 130.063 | 0.89 |
| 3-methoxy-4-hydroxymandelic acid (VMA) | C9H10O5 | 198.053 | 0.90 |
| 4-hydroxy-3-methoxyphenylglycol | C9H12O4 | 184.074 | 0.90 |
| adenosine-monophosphate | C10H14N5O7P | 347.063 | 0.90 |
| homogentisic acid | C8H8O4 | 168.042 | 0.90 |
| uridine | C9H12N2O6 | 244.070 | 0.90 |
| citramalic acid | C5H8O5 | 148.037 | 0.94 |
| propionylglycine | C5H9NO3 | 131.058 | 0.95 |
| deoxyguanosine-monophosphate | C10H14N5O7P | 347.063 | 1.00 |
| n-acetylalanine | C5H9NO3 | 131.058 | 1.00 |
| thymidine-monophosphate | C10H15N2O8P | 322.057 | 1.00 |
| methylmalonic acid | C4H6O4 | 118.027 | 1.05 |
| xanthine | C5H4N4O2 | 152.033 | 1.05 |
| aconitic acid | C6H6O6 | 174.016 | 1.07 |
| pyridoxal-phosphate | C8H10NO6P | 247.025 | 1.07 |
| itaconic acid | C5H6O4 | 130.027 | 1.10 |
| 3-hydroxymethylglutaric acid | C6H10O5 | 162.053 | 1.13 |
| succinate semialdehyde | C4H6O3 | 102.032 | 1.15 |
| 2-hydroxybutyric acid | C4H8O3 | 104.047 | 1.18 |
| deoxyuridine | C9H12N2O5 | 228.075 | 1.23 |

TABLE 3-continued

Metabolite library
Authentic standards were injected to generate a retention time library for this method.

| Name | Formula | Mass | Retention Time, min |
|---|---|---|---|
| deoxyadenosine monophosphate | C10H14N5O6P | 331.068 | 1.25 |
| thymine | C5H6N2O2 | 126.043 | 1.25 |
| 2,4-dihydroxypteridine | C6H4N4O2 | 164.033 | 1.27 |
| n-acetylcysteine | C5H9NO3S | 163.030 | 1.30 |
| 4-acetamidobutanoic acid | C6H11NO3 | 145.074 | 1.32 |
| n-methylaspartic acid | C5H9NO4 | 147.053 | 1.32 |
| mevalonolactone | C6H10O3 | 130.063 | 1.37 |
| 2-methylcitric acid | C7H10O7 | 206.043 | 1.41 |
| 6-hydroxynicotinic acid | C6H5NO3 | 139.027 | 1.43 |
| 2,6-dihydroxypyridine | C5H5NO2 | 111.032 | 1.45 |
| citicoline | C14H26N4O11P2 | 488.107 | 1.47 |
| acetoin | C4H8O2 | 88.052 | 1.56 |
| glutaric acid | C5H8O4 | 132.042 | 1.58 |
| hydroxyproline | C5H9NO3 | 131.058 | 1.60 |
| cyclic guanosine monophosphate | C10H12N5O7P | 345.047 | 1.62 |
| aspartic acid | C4H7NO4 | 133.038 | 1.66 |
| s-carboxymethylcysteine | C5H9NO4S | 179.025 | 1.67 |
| cyclic adenosine monophosphate | C10H12N5O6P | 329.053 | 1.69 |
| inosine | C10H12N4O5 | 268.081 | 1.70 |
| n-methylglutamic acid | C6H11NO4 | 161.069 | 1.72 |
| 4-pyridoxic acid | C8H9NO4 | 183.053 | 1.75 |
| isobutyrylglycine | C6H11NO3 | 145.074 | 1.79 |
| 2-hydroxypyridine | C5H5NO | 95.037 | 1.86 |
| butyrylglycine | C6H11NO3 | 145.074 | 1.97 |
| dimethylglycine | C4H9NO2 | 103.063 | 2.10 |
| methylsuccinic acid | C5H8O4 | 132.042 | 2.15 |
| asparagine | C4H8N2O3 | 132.053 | 2.20 |
| sarcosine | C3H7NO2 | 89.048 | 2.20 |
| serine | C3H7NO3 | 105.043 | 2.20 |
| threonine | C4H9NO3 | 119.058 | 2.20 |
| allothreonine | C4H9NO3 | 119.058 | 2.24 |
| hypoxanthine | C5H4N4O | 136.039 | 2.35 |
| ethylmalonic acid | C5H8O4 | 132.042 | 2.40 |
| glutamic acid | C5H9NO4 | 147.053 | 2.40 |
| xanthosine | C10H12N4O6 | 284.076 | 2.41 |
| glutamine | C5H10N2O3 | 146.069 | 2.50 |
| 3,4-dihydroxybenzoic acid | C7H6O4 | 154.027 | 2.57 |
| pyrocatechol | C6H6O2 | 110.037 | 2.57 |
| succinylacetone | C7H10O4 | 158.058 | 2.60 |
| homoserine | C4H9NO3 | 119.058 | 2.65 |
| thymidine | C10H14N2O5 | 242.090 | 2.82 |
| ophthalmic acid | C11H19N3O6 | 289.127 | 2.85 |
| 2-hydroxy-3-methylbutyric acid | C5H10O3 | 118.063 | 2.90 |
| 2-aminoadipic acid | C6H11NO4 | 161.069 | 2.95 |
| glycine | C2H5NO2 | 75.032 | 2.95 |
| betaine | C5H11NO2 | 117.079 | 3.00 |
| indoxyl sulfate | C8H7NO4S | 213.010 | 3.00 |
| 2-hydroxy-4-(methylthio)butanoic acid | C5H10O3S | 150.035 | 3.03 |
| proline | C5H9NO2 | 115.063 | 3.10 |
| o-succinyl-homoserine | C8H13NO6 | 219.074 | 3.14 |
| n-formyl-l-methionine | C6H11NO3S | 177.046 | 3.34 |
| n-acetylproline | C7H11NO3 | 157.074 | 3.36 |
| alanine | C3H7NO2 | 89.048 | 3.40 |
| 4-quinolinecarboxylic acid | C10H7NO2 | 173.048 | 3.46 |
| cyanocobalamin | C63H89CoN14O14P | 1355.575 | 3.47 |
| glycerol 3-phosphate | C3H9O6P | 172.014 | 3.47 |
| pantothenic acid | C9H17NO5 | 219.111 | 3.53 |
| 3-hydroxybenzyl alcohol | C7H8O2 | 124.052 | 3.68 |
| guaiacol | C7H8O2 | 124.052 | 3.68 |
| histidinol | C6H11N3O | 141.090 | 3.70 |
| 3,4-dihydroxyphenylacetic acid | C8H8O4 | 168.042 | 3.73 |
| guanosine | C10H13N5O5 | 283.092 | 3.76 |
| methylglutaric acid | C6H10O4 | 146.058 | 3.83 |
| adipic acid | C6H10O4 | 146.058 | 3.86 |
| 2-aminobutyric acid | C4H9NO2 | 103.063 | 3.89 |
| 2-methylbutyrylglycine | C7H13NO3 | 159.090 | 3.91 |
| mandelic acid | C8H8O3 | 152.047 | 4.00 |
| 2-aminoisobutyric acid | C4H9NO2 | 103.063 | 4.10 |
| tiglylglycine | C7H11NO3 | 157.074 | 4.15 |
| 3-methyl-2-oxovaleric acid | C6H10O3 | 130.063 | 4.36 |
| heptanoic acid | C7H14O2 | 130.099 | 4.36 |
| hydroquinone | C6H6O2 | 110.037 | 4.40 |
| 4-hydroxybenzoic acid | C7H6O3 | 138.032 | 4.45 |
| nicotinic acid | C6H5NO2 | 123.032 | 4.45 |

TABLE 3-continued

Metabolite library
Authentic standards were injected to generate a retention time library for this method.

| Name | Formula | Mass | Retention Time, min |
|---|---|---|---|
| isovalerylglycine | C7H13NO3 | 159.090 | 4.46 |
| 2,5-dihydroxybenzoic acid | C7H6O4 | 154.027 | 4.48 |
| 3-methylcrotonylglycine | C7H11NO3 | 157.074 | 4.52 |
| 4-hydroxyphenylacetic acid | C8H8O3 | 152.047 | 4.59 |
| citrulline | C6H13N3O3 | 175.096 | 4.60 |
| l-dopa | C9H11NO4 | 197.069 | 4.65 |
| 1-aminocyclopropanecarboxylic acid | C4H7NO2 | 101.048 | 4.70 |
| n-acetylmethionine | C7H13NO3S | 191.062 | 4.76 |
| theobromine | C7H8N4O2 | 180.065 | 4.78 |
| valine | C5H11NO2 | 117.080 | 4.79 |
| guanidinosuccinic acid | C5H9N3O4 | 175.059 | 4.80 |
| glucosamine | C6H13NO5 | 179.079 | 5.05 |
| d-mannosamine | C6H13NO5 | 179.079 | 5.10 |
| valerylglycine | C7H13NO3 | 159.090 | 5.20 |
| galactosamine | C6H13NO5 | 179.079 | 5.20 |
| methionine | C5H11NO2S | 149.051 | 5.22 |
| 2-acetamido-2-deoxy-beta-d-glucosylamine | C8H16N2O5 | 220.106 | 5.36 |
| trigonelline | C7H7NO2 | 137.048 | 5.69 |
| cysteine | C3H7NO2S | 121.020 | 5.78 |
| hippuric acid | C9H9NO3 | 179.058 | 5.80 |
| 4-hydroxybenzaldehyde | C7H6O2 | 122.037 | 5.84 |
| 2,3-dihydroxybenzoic acid | C7H6O4 | 154.027 | 5.90 |
| 3-hydroxybenzoic acid | C7H6O3 | 138.032 | 5.94 |
| phenylpyruvic acid | C9H8O3 | 164.047 | 6.00 |
| theophylline | C7H8N4O2 | 180.065 | 6.00 |
| paraxanthine | C7H8N4O2 | 180.065 | 6.07 |
| pipecolic acid | C6H11NO2 | 129.079 | 6.10 |
| tyrosine | C9H11NO3 | 181.074 | 6.25 |
| salicylamide | C7H7NO2 | 137.048 | 6.40 |
| beta-alanine | C3H7NO2 | 89.048 | 6.58 |
| xanthurenic acid | C10H7NO4 | 205.038 | 6.58 |
| n-acetylserotonin | C12H14N2O2 | 218.106 | 6.60 |
| homocitrulline | C7H15N3O3 | 189.111 | 6.62 |
| caffeic acid | C9H8O4 | 180.042 | 6.75 |
| n-acetylornithine | C7H14N2O3 | 174.100 | 6.79 |
| 6-carboxyhexanoic acid | C7H12O4 | 160.074 | 6.99 |
| indole-3-acetamide | C10H10N2O | 174.079 | 7.02 |
| homovanillic acid | C9H10O4 | 182.058 | 7.20 |
| 4-aminobenzoic acid | C7H7NO2 | 137.048 | 7.24 |
| kynurenic acid | C10H7NO3 | 189.043 | 7.27 |
| 3-hydroxyanthranilic acid | C7H7NO3 | 153.043 | 7.29 |
| 5-aminolevulinic acid | C5H9NO3 | 131.058 | 7.30 |
| suberylglycine | C10H17NO5 | 231.111 | 7.30 |
| 2-quinolinecarboxylic acid | C10H7NO2 | 173.048 | 7.34 |
| creatine | C4H9N3O2 | 131.069 | 7.50 |
| guanidinoacetic acid | C3H7N3O2 | 117.054 | 7.50 |
| caffeine | C8H10N4O2 | 194.080 | 7.53 |
| pterin | C6H5N5O | 163.049 | 7.53 |
| dihydrobiopterin | C9H13N5O3 | 239.102 | 7.62 |
| alloisoleucine | C6H13NO2 | 131.095 | 7.60 |
| 4-aminobutyric acid | C4H9NO2 | 103.063 | 7.75 |
| biotin | C10H16N2O3S | 244.088 | 7.77 |
| 3-methoxytyrosine | C10H13NO4 | 211.084 | 7.84 |
| 3-aminoisobutyric acid | C4H9NO2 | 103.063 | 8.05 |
| 4-coumaric acid | C9H8O3 | 164.047 | 8.20 |
| thiopurine s-methylether | C6H6N4S | 166.031 | 8.23 |
| n-alpha-acetyllysine | C8H16N2O3 | 188.116 | 8.25 |
| hexanoylglycine | C8H15NO3 | 173.105 | 8.30 |
| n-acetylphenylalanine | C11H13NO3 | 207.090 | 8.58 |
| isoleucine | C6H13NO2 | 131.095 | 8.50 |
| leucine | C6H13NO2 | 131.095 | 8.50 |
| phenylpropionylglycine | C11H13NO3 | 207.090 | 8.64 |
| 2',4'-dihydroxyacetophenone | C8H8O3 | 152.047 | 8.69 |
| 4-imidazoleacetic acid | C5H6N2O2 | 126.043 | 8.70 |
| 3-(2-hydroxyphenyl)propanoic acid | C9H10O3 | 166.063 | 8.73 |
| salicylic acid | C7H6O3 | 138.032 | 8.78 |
| riboflavin | C17H20N4O6 | 376.138 | 8.80 |
| n-acetyltryptophan | C13H14N2O3 | 246.100 | 8.90 |
| suberic acid | C8H14O4 | 174.089 | 8.98 |
| dethiobiotin | C10H18N2O3 | 214.132 | 9.00 |
| indoleacetaldehyde | C10H9NO | 159.068 | 9.00 |
| indole-3-ethanol | C10H11NO | 161.084 | 9.05 |
| melatonin | C13H16N2O2 | 232.121 | 9.26 |
| 3-methyl-2-oxindole | C9H9NO | 147.068 | 9.37 |

TABLE 3-continued

Metabolite library
Authentic standards were injected to generate a retention time library for this method.

| Name | Formula | Mass | Retention Time, min |
| --- | --- | --- | --- |
| norleucine | C6H13NO2 | 131.095 | 9.50 |
| trans-cinnamaldehyde | C9H8O | 132.058 | 9.58 |
| cytidine | C9H13N3O5 | 243.086 | 9.60 |
| rosmarinic acid | C18H16O8 | 360.085 | 9.61 |
| lipoamide | C8H15NOS2 | 205.060 | 9.66 |
| trans-cinnamic acid | C9H8O2 | 148.052 | 9.70 |
| heptanoylglycine | C9H17NO3 | 187.121 | 9.73 |
| azelaic acid | C9H16O4 | 188.105 | 9.77 |
| adenosine | C10H13N5O4 | 267.097 | 9.80 |
| folate | C19H19N7O6 | 441.140 | 9.80 |
| 3-nitro-l-tyrosine | C9H10N2O5 | 226.059 | 10.00 |
| carnitine | C7H15NO3 | 161.105 | 10.00 |
| deoxyadenosine | C10H13N5O3 | 251.102 | 10.00 |
| guanine | C5H5N5O | 151.049 | 10.00 |
| indole-3-methyl acetic acid | C11H11NO2 | 189.079 | 10.00 |
| nicotinamide | C6H6N2O | 122.048 | 10.00 |
| phenylalanine | C9H11NO2 | 165.079 | 10.00 |
| 5-hydroxytryptophan | C11H12N2O3 | 220.085 | 10.01 |
| succinylcarnitine | C11H19NO6 | 261.121 | 10.01 |
| glutarylcarnitine | C12H21NO6 | 275.137 | 10.09 |
| 1-methyladenosine | C11H15N5O4 | 281.112 | 10.10 |
| octanoylglycine | C10H19NO3 | 201.136 | 10.17 |
| deoxycytidine | C9H13N3O4 | 227.091 | 10.17 |
| methylthioadenosine | C11H15N5O3S | 297.090 | 10.17 |
| tryptophan | C11H12N2O2 | 204.090 | 10.20 |
| 3-hydroxyisovalerylcarnitine | C12H23NO5 | 261.158 | 10.23 |
| 6-hydroxydopamine | C8H11NO3 | 169.074 | 10.24 |
| noradrenaline | C8H11NO3 | 169.074 | 10.24 |
| trans-cyclohexanediol | C6H12O2 | 116.084 | 10.24 |
| urocanate | C6H6N2O2 | 138.043 | 10.24 |
| 3,5-diiodo-l-tyrosine | C9H9I2NO3 | 432.867 | 10.25 |
| butyric acid | C4H8O2 | 88.052 | 10.25 |
| diethanolamine | C4H11NO2 | 105.079 | 10.25 |
| isobutyric acid | C4H8O2 | 88.052 | 10.25 |
| sebacic acid | C10H18O4 | 202.121 | 10.25 |
| cortisone | C21H28O5 | 360.194 | 10.29 |
| acetylcarnitine | C9H17NO4 | 203.116 | 10.30 |
| kynurenine | C10H12N2O3 | 208.085 | 10.32 |
| 2-methylpropanal | C4H8O | 72.058 | 10.33 |
| 10-hydroxydecanoic acid | C10H20O3 | 188.141 | 10.37 |
| pyridoxal | C8H9NO3 | 167.058 | 10.39 |
| epinephrine | C9H13NO3 | 183.090 | 10.40 |
| adenine | C5H5N5 | 135.054 | 10.42 |
| cortisol | C21H30O5 | 362.209 | 10.42 |
| thyrotropin releasing hormone | C16H22N6O4 | 362.170 | 10.48 |
| methyl 4-aminobutyric acid | C5H11NO2 | 117.079 | 10.51 |
| propionylcarnitine | C10H19NO4 | 217.131 | 10.54 |
| cytosine | C4H5N3O | 111.043 | 10.59 |
| 3,5-diiodo-l-thyronine | C15H13I2NO4 | 524.893 | 10.60 |
| cystine | C6H12N2O4S2 | 240.024 | 10.60 |
| n-acetylputrescine | C6H14N2O | 130.111 | 10.60 |
| normetanephrine | C9H13NO3 | 183.090 | 10.60 |
| deoxycarnitine | C7H15NO2 | 145.110 | 10.66 |
| pyridoxine | C8H11NO3 | 169.074 | 10.66 |
| 4-guanidinobutanoic acid | C5H11N3O2 | 145.085 | 10.70 |
| corticosterone | C21H30O4 | 346.214 | 10.70 |
| 2-aminophenol | C6H7NO | 109.053 | 10.75 |
| 1-hydroxy-2-naphthoic acid | C11H8O3 | 188.047 | 10.77 |
| butyrylcarnitine | C11H21NO4 | 231.147 | 10.77 |
| cortisol 21-acetic acid | C23H32O6 | 404.220 | 10.78 |
| cortexolone | C21H30O4 | 346.214 | 10.80 |
| dopamine | C8H11NO2 | 153.079 | 10.80 |
| n-acetylleucine | C8H15NO3 | 173.105 | 10.83 |
| creatinine | C4H7N3O | 113.059 | 10.85 |
| isovalerylcarnitine | C12H23NO4 | 254.219 | 10.90 |
| homocysteine thiolactone | C4H7NOS | 117.025 | 10.90 |
| 5-methylcytosine | C5H7N3O | 125.059 | 10.95 |
| methionine sulfoximine | C5H12N2O3S | 180.057 | 10.95 |
| liothyronine | C15H12I3NO4 | 650.790 | 10.96 |
| saccharopine | C11H20N2O6 | 276.132 | 11.03 |
| omega-hydroxydodecanoic acid | C12H24O3 | 216.173 | 11.05 |
| tyramine | C8H11NO | 137.084 | 11.08 |
| 3-hydroxyphenylacetic acid | C8H8O3 | 152.047 | 11.13 |
| methylguanidine | C2H7N3 | 73.064 | 11.16 |

TABLE 3-continued

Metabolite library
Authentic standards were injected to generate a retention time library for this method.

| Name | Formula | Mass | Retention Time, min |
|---|---|---|---|
| thyroxine | C15H11I4NO4 | 776.687 | 11.18 |
| pregnenolone sulfate | C21H32O5S | 396.197 | 11.25 |
| salsolinol | C10H13NO2 | 179.095 | 11.25 |
| 3-methoxytyramine | C9H13NO2 | 167.095 | 11.30 |
| gamma,gamma-dimethylallyl pyrophosphate | C5H12O7P2 | 246.006 | 11.33 |
| cystathionine | C7H14N2O4S | 222.067 | 11.35 |
| glycocholic acid | C26H43NO6 | 465.309 | 11.37 |
| phenylacetaldehyde | C8H8O | 120.058 | 11.40 |
| deoxycorticosterone acetic acid | C23H32O4 | 372.230 | 11.42 |
| phenylethanolamine | C8H11NO | 137.084 | 11.42 |
| octanoylcarnitine | C15H29NO4 | 287.210 | 11.47 |
| biliverdin | C33H34N4O6 | 582.248 | 11.50 |
| lumichrome | C12H10N4O2 | 242.080 | 11.58 |
| glycochenodeoxycholic acid | C26H43NO5 | 449.314 | 11.63 |
| lithocholyltaurine | C26H45NO5S | 483.302 | 11.65 |
| lauric acid | C12H24O2 | 200.178 | 11.66 |
| pyruvic aldehyde | C3H4O2 | 72.021 | 11.66 |
| cholic acid | C24H40O5 | 408.288 | 11.70 |
| s-adenosylhomocysteine | C14H20N6O5S | 384.122 | 11.74 |
| decanoylcarnitine | C17H33NO4 | 315.241 | 11.77 |
| serotonin | C10H12N2O | 176.095 | 11.80 |
| ethyl 3-indoleacetic acid | C12H13NO2 | 203.095 | 11.82 |
| phenethylamine | C8H11N | 121.089 | 11.82 |
| gamma-linolenic acid | C18H30O2 | 278.225 | 11.86 |
| chenodeoxycholic acid | C24H40O4 | 392.293 | 11.94 |
| linoleic acid | C18H32O2 | 280.240 | 11.95 |
| l-tryptophanamide | C11H13N3O | 203.106 | 11.98 |
| deoxycholic acid | C24H40O4 | 392.293 | 11.99 |
| homocystine | C8H16N2O4S2 | 268.055 | 12.00 |
| lithocholic acid | C24H40O3 | 376.298 | 12.00 |
| quinoline | C9H7N | 129.058 | 12.00 |
| ursodeoxycholic acid | C24H40O4 | 392.293 | 12.00 |
| dodecanoylcarnitine | C19H37NO4 | 343.272 | 12.10 |
| 1-methylnicotinamide | C7H9N2O | 137.071 | 12.11 |
| alpha-tocopherol | C29H50O2 | 430.381 | 12.11 |
| glycerol-myristic acid | C17H34O4 | 302.246 | 12.14 |
| beta-carotene | C40H56 | 536.438 | 12.17 |
| palmitic acid | C16H32O2 | 256.240 | 12.20 |
| n-methyltryptamine | C11H14N2 | 174.116 | 12.22 |
| 3-methyladenine | C6H7N5 | 149.070 | 12.25 |
| heptadecanoic acid | C17H34O2 | 270.256 | 12.26 |
| 2-undecanone | C11H22O | 170.167 | 12.29 |
| dodecanoylglycine | C14H27NO3 | 257.199 | 12.29 |
| 5-valerolactone | C5H8O2 | 100.052 | 12.30 |
| tryptamine | C10H12N2 | 160.100 | 12.30 |
| deoxyguanosine | C10H13N5O4 | 267.097 | 12.31 |
| pentanoic acid | C5H10O2 | 102.068 | 12.32 |
| retinoic acid | C20H28O2 | 300.209 | 12.35 |
| diaminopimelic acid | C7H14N2O4 | 190.095 | 12.38 |
| 3-hydroxypalmitoylcarnitine | C23H45NO5 | 415.330 | 12.40 |
| didecanoyl-glycerophosphocholine | C28H56NO8P | 565.374 | 12.41 |
| porphobilinogen | C10H14N2O4 | 226.095 | 12.44 |
| n,n-dimethyl-1,4-phenylenediamine | C8H12N2 | 136.100 | 12.45 |
| 25-hydroxyvitamin d (calcidiol) | C27H44O2 | 400.334 | 12.47 |
| retinol | C20H30O | 286.230 | 12.50 |
| oleoyl-glycerol | C21H40O4 | 356.293 | 12.52 |
| docosahexaenoic acid | C22H32O2 | 328.240 | 12.55 |
| 25-hydroxycholesterol | C27H46O2 | 402.350 | 12.56 |
| desmosterol | C27H44O | 384.339 | 12.56 |
| nervonic acid | C24H46O2 | 366.350 | 12.56 |
| elaidic acid | C18H34O2 | 282.256 | 12.60 |
| palmitoylcarnitine | C23H45NO4 | 399.335 | 12.61 |
| lanosterol | C30H50O | 426.386 | 12.64 |
| 7-dehydrocholesterol | C27H44O | 384.339 | 12.65 |
| arachidic acid | C20H40O2 | 312.303 | 12.72 |
| octadecanoylcarnitine | C25H49NO4 | 427.366 | 12.83 |
| erucic acid | C22H42O2 | 338.318 | 12.83 |
| argininosuccinic acid | C10H18N4O6 | 290.123 | 12.84 |
| 5,6 dimethylbenzimidazole | C9H10N2 | 146.084 | 12.89 |
| sphinganine | C18H39NO2 | 301.298 | 12.90 |
| bis(2-ethylhexyl)phthalate | C24H38O4 | 390.277 | 12.93 |
| 1-phenylethanol | C8H10O | 122.073 | 12.95 |
| protoporphyrin | C34H34N4O4 | 562.258 | 13.40 |
| nicotine | C10H14N2 | 162.116 | 14.50 |

TABLE 3-continued

Metabolite library
Authentic standards were injected to generate a retention time library for this method.

| Name | Formula | Mass | Retention Time, min |
|---|---|---|---|
| retinyl palmitic acid | C36H60O2 | 524.459 | 15.40 |
| histidine | C6H9N3O2 | 155.069 | 16.80 |
| 1-methylhistidine | C7H11N3O2 | 169.085 | 16.90 |
| 3-methylhistidine | C7H11N3O2 | 169.085 | 16.90 |
| n,n-dimethyl-arginine | C8H18N4O2 | 202.143 | 17.00 |
| 5-hydroxylysine | C6H14N2O3 | 162.100 | 17.05 |
| lysine | C6H14N2O2 | 146.106 | 17.10 |
| ornithine | C5H12N2O2 | 132.090 | 17.10 |
| n,n,n-trimethyllysine | C9H20N2O2 | 188.152 | 17.20 |
| arginine | C6H14N4O2 | 174.112 | 17.30 |

Ion feature identifications from one representative (a) plasma or (b) urine QC sample were made by searching the library of authentic standards (Table 3) using MassHunter Qualitative. The peak height filter was set to 2,000, the allowable retention time error was set to ±0.3 minutes, and the allowable mass error was set to ±10 ppm.

TABLE 4

Metabolites detected in human samples

| ID - Plasma | RT, min | Area |
|---|---|---|
| *Identifications of the plasma QC sample.* | | |
| pyruvic acid | 0.5 | 2.45E+05 |
| isocitric acid | 0.5 | 6.59E+05 |
| malic acid | 0.5 | 5.60E+05 |
| maleic acid | 0.6 | 6.25E+04 |
| 2-ketoglutaric acid | 0.6 | 3.98E+05 |
| lactic acid | 0.7 | 2.58E+06 |
| n-acetylaspartic acid | 0.7 | 3.31E+04 |
| citric acid | 0.7 | 1.20E+06 |
| 2-methylmaleic acid | 0.7 | 8.51E+04 |
| uric acid | 0.7 | 1.05E+06 |
| pyroglutamic acid | 0.8 | 2.16E+05 |
| succinic acid | 0.9 | 1.15E+05 |
| uridine | 0.9 | 3.33E+04 |
| propionylglycine | 1.0 | 1.93E+04 |
| methylmalonic acid | 1.0 | 4.44E+05 |
| xanthine | 1.0 | 7.13E+04 |
| itaconic acid | 1.1 | 2.77E+04 |
| 2-hydroxybutyric acid | 1.1 | 2.21E+05 |
| hydroxyproline | 1.6 | 5.17E+06 |
| aspartic acid | 1.7 | 4.49E+04 |
| butyrylglycine | 2.1 | 3.98E+05 |
| asparagine | 2.2 | 8.25E+05 |
| serine | 2.2 | 2.53E+05 |
| dimethylglycine | 2.3 | 1.49E+06 |
| hypoxanthine | 2.3 | 1.92E+06 |
| threonine | 2.4 | 1.19E+06 |
| glutamic acid | 2.4 | 8.87E+05 |
| glutamine | 2.5 | 8.07E+06 |
| glycine | 3.0 | 1.73E+04 |
| betaine | 3.0 | 3.97E+07 |
| proline | 3.1 | 2.34E+07 |
| pantothenic acid | 3.3 | 1.48E+05 |
| alanine | 3.3 | 1.40E+06 |
| 2-aminobutyric acid | 3.9 | 9.76E+04 |
| citrulline | 4.5 | 4.23E+05 |
| theobromine | 4.5 | 7.27E+04 |
| methionine | 5.2 | 7.43E+04 |
| phenylpyruvic acid | 6.2 | 1.06E+05 |
| tyrosine | 6.2 | 1.51E+05 |
| alloisoleucine | 7.6 | 1.20E+06 |
| creatine | 7.6 | 6.99E+06 |
| isoleucine/leucine | 8.4 | 4.92E+06 |
| suberic acid | 9.0 | 1.25E+05 |
| trans-cinnamaldehyde | 9.6 | 8.25E+04 |
| trans-cinnamic acid | 9.7 | 8.30E+04 |
| azelaic acid | 9.8 | 9.34E+05 |
| phenylalanine | 10.0 | 1.19E+06 |
| nicotinamide | 10.0 | 1.38E+05 |
| carnitine | 10.1 | 3.83E+07 |
| deoxyadenosine | 10.2 | 2.73E+05 |
| 3-hydroxyisovalerylcarnitine | 10.2 | 4.79E+04 |
| tryptophan | 10.2 | 2.32E+05 |
| sebacic acid | 10.3 | 1.55E+05 |
| 1-methyladenosine | 10.3 | 9.27E+04 |
| isobutyric acid | 10.3 | 6.77E+05 |
| diethanolamine | 10.3 | 7.41E+05 |
| acetylcarnitine | 10.3 | 2.04E+07 |
| propionylcarnitine | 10.5 | 5.23E+06 |
| n-acetylputrescine | 10.6 | 8.15E+04 |
| deoxycarnitine | 10.7 | 3.98E+06 |
| butyrylcarnitine | 10.8 | 4.37E+05 |
| creatinine | 10.8 | 1.38E+07 |
| glycocholic acid | 11.4 | 1.74E+05 |
| phenylacetaldehyde | 11.4 | 5.15E+05 |
| phenylethanolamine | 11.4 | 3.82E+05 |
| octanoylcarnitine | 11.5 | 8.27E+05 |
| biliverdin | 11.5 | 2.61E+04 |
| glycochenodeoxycholic acid | 11.6 | 1.24E+05 |
| decanoylcarnitine | 11.8 | 2.41E+06 |
| linoleic acid | 12.0 | 4.34E+05 |
| lithocholic acid | 12.0 | 6.43E+04 |
| dodecanoylcarnitine | 12.1 | 3.20E+05 |
| glycerol-myristic acid | 12.1 | 1.57E+05 |
| palmitic acid | 12.2 | 2.23E+05 |
| heptadecanoic acid | 12.3 | 3.79E+05 |
| docosahexaenoic acid | 12.5 | 2.23E+04 |
| oleoyl-glycerol | 12.5 | 8.02E+05 |
| palmitoylcarnitine | 12.6 | 1.27E+06 |
| arachidic acid | 12.7 | 7.53E+04 |
| erucic acid | 12.8 | 7.63E+04 |
| octadecanoylcarnitine | 12.8 | 3.91E+05 |
| 1-phenylethanol | 13.0 | 8.32E+05 |
| histidine | 16.9 | 8.16E+05 |
| n,n-dimethyl-arginine | 17.0 | 1.95E+05 |
| ornithine | 17.1 | 7.05E+05 |
| lysine | 17.1 | 8.96E+05 |
| n,n,n-trimethyllysine | 17.3 | 1.64E+05 |
| arginine | 17.3 | 2.90E+06 |
| *Identifications of the urine QC sample* | | |
| 2-propenoic acid | 0.6 | 6.85E+04 |
| maleic acid | 0.6 | 5.86E+05 |
| lactic acid | 0.7 | 2.04E+05 |
| n-acetylaspartic acid | 0.7 | 1.20E+06 |
| 2-oxoadipic acid | 0.7 | 4.35E+04 |
| citric acid | 0.7 | 8.64E+06 |
| pyruvic acid | 0.7 | 1.44E+05 |
| 2-methylmaleic acid | 0.8 | 4.17E+06 |

TABLE 4-continued

Metabolites detected in human samples

| ID - Plasma | RT, min | Area |
|---|---|---|
| uric acid | 0.8 | 1.26E+05 |
| propionylglycine | 0.9 | 4.21E+04 |
| n-acetylglutamic acid | 0.9 | 2.07E+05 |
| succinic acid | 0.9 | 2.38E+06 |
| citramalic acid | 1.0 | 2.83E+06 |
| fumaric acid | 1.0 | 7.47E+03 |
| homogentisic acid | 1.0 | 1.44E+04 |
| methylmalonic acid | 1.1 | 3.69E+05 |
| xanthine | 1.1 | 5.14E+04 |
| aconitic acid | 1.1 | 2.85E+05 |
| itaconic acid | 1.1 | 4.57E+05 |
| 3-hydroxymethylglutaric acid | 1.1 | 1.95E+06 |
| succinate semialdehyde | 1.1 | 4.16E+04 |
| 2-hydroxybutyric acid | 1.2 | 3.12E+05 |
| n-acetylcysteine | 1.3 | 1.35E+04 |
| 4-acetamidobutanoic acid | 1.4 | 6.80E+05 |
| 2-methylcitric acid | 1.4 | 1.65E+06 |
| acetoin | 1.6 | 1.14E+04 |
| glutaric acid | 1.6 | 8.04E+04 |
| 2-hydroxypyridine | 1.6 | 2.89E+04 |
| 6-hydroxynicotinic acid | 1.6 | 6.97E+05 |
| cyclic adenosine monophosphate | 1.7 | 7.58E+03 |
| 4-pyridoxic acid | 1.8 | 7.48E+06 |
| isobutyrylglycine | 1.8 | 8.92E+04 |
| methylsuccinic acid | 2.2 | 9.70E+04 |
| serine | 2.2 | 4.90E+04 |
| threonine | 2.3 | 2.89E+04 |
| hypoxanthine | 2.3 | 8.00E+04 |
| glutamic acid | 2.3 | 1.19E+05 |
| ethylmalonic acid | 2.4 | 2.67E+06 |
| xanthosine | 2.4 | 4.99E+04 |
| glutamine | 2.5 | 8.13E+05 |
| 2-aminoadipic acid | 2.9 | 1.43E+05 |
| betaine | 2.9 | 2.59E+04 |
| 2-hydroxy-3-methylbutyric acid | 2.9 | 8.80E+04 |
| indoxyl sulfuric acid | 2.9 | 3.55E+06 |
| alanine | 3.5 | 2.39E+04 |
| pantothenic acid | 3.5 | 1.54E+06 |
| 3-hydroxybenzyl alcohol | 3.8 | 5.43E+04 |
| adipic acid | 3.9 | 4.61E+05 |
| 2-methylbutyrylglycine | 3.9 | 1.52E+05 |
| mandelic acid | 4.0 | 3.91E+04 |
| tiglylglycine | 4.2 | 1.48E+05 |
| citrulline | 4.4 | 5.52E+04 |
| isovalerylglycine | 4.5 | 3.13E+05 |
| 3-methylcrotonylglycine | 4.5 | 2.28E+06 |
| guanidinosuccinic acid | 4.6 | 5.52E+04 |
| 4-hydroxyphenyllactic acid | 4.6 | 4.63E+06 |
| 2,5-dihydroxybenzoic acid | 4.7 | 5.65E+05 |
| hippuric acid | 5.8 | 9.32E+06 |
| 4-hydroxybenzaldehyde | 5.9 | 2.80E+05 |
| kynurenic acid | 7.3 | 1.02E+04 |
| creatine | 7.6 | 3.60E+05 |
| guanidinoacetic acid | 7.7 | 4.54E+04 |
| hexanoylglycine | 8.3 | 4.55E+05 |
| n-alpha-acetyllysine | 8.4 | 1.40E+05 |
| salicylic acid | 8.8 | 2.40E+04 |
| n-acetyltryptophan | 8.9 | 2.56E+04 |
| suberic acid | 9.0 | 3.17E+05 |
| azelaic acid | 9.8 | 5.10E+05 |
| 1-methyladenosine | 10.2 | 2.46E+04 |
| urocanic acid | 10.2 | 2.20E+05 |
| octanoylglycine | 10.3 | 5.67E+04 |
| pyridoxal | 10.4 | 1.51E+04 |
| adenine | 10.5 | 6.43E+04 |
| cystine | 10.7 | 1.35E+04 |
| 4-guanidinobutanoic acid | 10.7 | 2.57E+04 |
| creatinine | 10.8 | 1.42E+05 |
| saccharopine | 11.1 | 2.44E+04 |
| histidine | 16.8 | 1.78E+06 |
| 1-methylhistidine | 16.9 | 1.52E+05 |
| n,n-dimethyl-arginine | 17.0 | 2.60E+04 |
| anserine | 17.4 | 1.03E+05 |
| carnosine | 17.4 | 5.22E+04 |

Among all plasma samples, compounds eluting between minutes 13 to 16 were searched for potential annotations using the HMDB and KEGG modules in Progenesis. Six potential results within 3 ppm mass error were found for a selected feature eluting at 14.47 min with a m/z of 844.5093.

TABLE 5

Search results of a non-polar compound in plasma

| ChemSpider ID | Description | Adducts | Formula | Mass error (ppm) | Isotope similarity |
|---|---|---|---|---|---|
| CSID35032656 | (19R,25S)-22,25,28,28-Tetrahydroxy-22,28-dioxido-16-oxo-17,21,23,27-tetraoxa-22lambda~5~,28lambda~5~-diphosphaoctacosan-19-yl (9Z,12Z)-9,12-octadecadienoate | M + NH4 | $C_{40}H_{76}O_{13}P_2$ | −0.85 | 88.73 |
| CSID35032669 | (7Z,19R,25S)-22,25,28,28-Tetrahydroxy-22,28-dioxido-16-oxo-17,21,23,27-tetraoxa-22lambda~5~,28lambda~5~-diphosphaoctacos-7-en-19-yl (11Z)-11-octadecenoate | M + NH4 | $C_{40}H_{76}O_{13}P_2$ | −0.85 | 88.73 |
| CSID35032670 | (7Z,19R,25S)-22,25,28,28-Tetrahydroxy-22,28-dioxido-16-oxo-17,21,23,27-tetraoxa-22lambda~5~,28lambda~5~-diphosphaoctacos-7-en-19-yl (9Z)-9-octadecenoate | M + NH4 | $C_{40}H_{76}O_{13}P_2$ | −0.85 | 88.73 |
| CSID35032696 | (2R,8S)-2-[(9Z)-9-Hexadecenoyloxy]-5,8,11,11-tetrahydroxy-5,11-dioxido-4,6,10-trioxa-5lambda~5~,11lambda~5~-diphosphaundec-1-yl (11Z)-11-octadecenoate | M + NH4 | $C_{40}H_{76}O_{13}P_2$ | −0.85 | 88.73 |
| CSID35032711 | (2R,8S)-2-[(9Z)-9-Hexadecenoyloxy]-5,8,11,11-tetrahydroxy-5,11-dioxido-4,6,10-trioxa-5lambda~5~,11lambda~5~-diphosphaundec-1-yl (9Z)-9-octadecenoate | M + NH4 | $C_{40}H_{76}O_{13}P_2$ | −0.85 | 88.73 |

TABLE 5-continued

Search results of a non-polar compound in plasma

| ChemSpider ID | Description | Adducts | Formula | Mass error (ppm) | Isotope similarity |
|---|---|---|---|---|---|
| CSID35032724 | (2R,8S)-5,8,11,11-Tetrahydroxy-5,11-dioxido-2-(palmitoyloxy)-4,6,10-trioxa-5lambda~5~,11lambda~5~-diphosphaundec-1-yl (9Z,12Z)-9,12-octadecadienoate | M + NH4 | $C_{40}H_{76}O_{13}P_2$ | −0.85 | 88.73 |

The CVs of select amino acids and acylcarnitines were calculated from the peak areas of 5 replicate injections of the plasma QC sample.

TABLE 6

Peak area precision of select plasma amino acids and acylcarnitines

| Compound | Mean Peak Area | CV, % |
|---|---|---|
| Glutamine | 8.1E+06 | 3.9 |
| Alanine | 1.5E+06 | 4.6 |
| Citrulline | 4.3E+05 | 1.7 |
| Methionine | 6.9E+04 | 6.9 |
| Alloisoleucine | 9.8E+05 | 6.8 |
| Isoleucine/Leucine | 4.8E+06 | 5.1 |
| Tryptophan | 2.3E+05 | 3.9 |
| Propionylcarnitine | 5.2E+06 | 3.3 |
| Palmitoylcarnitine | 1.2E+06 | 3.5 |
| Stearoylcarnitine | 3.7E+05 | 3.6 |

TABLE 7

A metabolomics analysis example of polar molecules, followed by less polar molecules, and then non-polar molecules.

| Compound Name | Retention Time (min) |
|---|---|
| Succinate | 2 |
| Methylmalonate (MMA) | 2.9 |
| Lactate | 3.9 |
| Glycine | 4.4 |
| Glutamate | 4.5 |
| allo-Isoleucine (Allo-Ile) | 5.6 |
| Ethyl Malonate | 6 |
| Isoleucine (Ile) | 6.2 |
| Leucine (Leu) | 6.6 |
| Glutarate | 8.5 |
| Tyrosine | 10.8 |
| Adipic Acid | 13.2 |
| 25-Hydroxy Vitamin D2 | 14.5 |
| Phenylalanine | 15.2 |
| Sebacic Acid | 17.9 |
| 25-Hydroxy Vitamin D3 | 21.8 |
| C4-Acylcarnitine | 22.4 |

As used herein, the singular terms "a," "an," and "the" include plural referents unless the context clearly dictates otherwise. Thus, for example, reference to an object can include multiple objects unless the context clearly dictates otherwise.

As used herein, the terms "substantially," "substantial," "approximately," and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, a first numerical value can be deemed to be "substantially" the same or equal to a second numerical value if the first numerical value is within a range of variation of less than or equal to ±10% of the second numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

While the disclosure has been described with reference to the specific embodiments thereof, it should be understood by those skilled in the art that various changes may be made and equivalents may be substituted without departing from the true spirit and scope of the disclosure as defined by the appended claim(s). In addition, many modifications may be made to adapt a particular situation, material, composition of matter, method, operation or operations, to the objective, spirit and scope of the disclosure. All such modifications are intended to be within the scope of the claim(s) appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations are not a limitation of the disclosure.

What is claimed is:

1. A method of analyzing a biological sample comprising:
    separating components of the biological sample via reversed-phase (RP) chromatography to obtain an elute;
    subsequently, subjecting the elute to separation via ion-exchange (IEX) chromatography or mixed-mode IEX chromatography; and
    detecting separated compounds to determine the components of the biological sample;

wherein:
the separating and the subjecting are conducted with one aqueous to organic solvent gradient; and
there is no switching valve between the RP chromatography and IEX chromatography.

2. The method of claim 1, wherein the biological sample is from a subject having or suspected of having a metabolic disruption.

3. The method of claim 1, wherein the biological sample is a plasma sample or a urine sample.

4. The method of claim 1, wherein the biological sample comprises lipids, carbohydrates, and metabolic intermediates.

5. The method of claim 1, wherein the biological sample comprises polar and non-polar metabolites.

6. The method of claim 1, wherein the detecting step is performed using mass spectrometry.

7. The method of claim 1, wherein the detecting step includes qualitative analysis.

8. The method of claim 1, wherein isomers of metabolites in the biological sample are separated.

9. The method of claim 1, wherein the biological sample comprises methylmalonic acid, glutamine, glycine, citrulline, methionine, alloisoleucine, arginine, creatine, carnitine, propionylcarnitine, stearoylcarnitine, 2-methylcitric acid, propionylglycine, 2-methylbutyrylglycine, 3-methylcrotonylglycine, adipic acid, suberic acid, and glutaric acid and wherein the detecting separated compounds comprises detecting the methylmalonic acid, glutamine, glycine, citrulline, methionine, alloisoleucine, arginine, creatine, carnitine, propionylcarnitine, stearoylcarnitine, 2-methylcitric acid, propionylglycine, 2-methylbutyrylglycine, 3-methylcrotonylglycine, adipic acid, suberic acid, and glutaric acid.

10. The method of claim 1, wherein the biological sample comprises plasma; and wherein the step of detecting comprises detecting 88 metabolites; and wherein the method is conducted in 20 minutes or less.

11. The method of claim 1, wherein the biological sample comprises urine, and wherein the step of detecting comprises detecting 82 metabolites; and wherein the method is conducted in 20 minutes or less.

* * * * *